(12) United States Patent
Tsuji et al.

(10) Patent No.: US 8,043,850 B2
(45) Date of Patent: Oct. 25, 2011

(54) FLUORESCENT PROTEIN AND GENE ENCODING THE SAME

(75) Inventors: Frederick I. Tsuji, San Diego, CA (US); Hiroshi Mizuno, Ibaraki (JP); Kenji Takase, Ibaraki (JP); Mitsuru Momma, Ibaraki (JP); Zui Fujimoto, Ibaraki (JP); Toshiyuki Wako, Ibaraki (JP); Yasuhiro Takenaka, Ibaraki (JP); Noboru Nakura, Toyama (JP); Hiromi Takenaka, Tokyo (JP)

(73) Assignees: NEC Soft, Ltd., Tokyo (JP); National Institute of Agrobiochemical Science, Ibaraki (JP)

( * ) Notice: Subject to any disclaimer, the term of this patent is extended or adjusted under 35 U.S.C. 154(b) by 340 days.

(21) Appl. No.: 12/204,557

(22) Filed: Sep. 4, 2008

(65) Prior Publication Data

US 2009/0123969 A1      May 14, 2009

Related U.S. Application Data

(60) Division of application No. 10/953,050, filed on Sep. 30, 2004, now Pat. No. 7,442,768, which is a continuation-in-part of application No. PCT/JP2004/004818, filed on Mar. 31, 2004.

(51) Int. Cl.
*C12N 15/00* (2006.01)
*C12Q 1/68* (2006.01)
*C12P 21/06* (2006.01)

(52) U.S. Cl. ........... 435/320.1; 435/6; 435/69.1; 514/44

(58) Field of Classification Search ........................ None
See application file for complete search history.

(56) References Cited

U.S. PATENT DOCUMENTS 5,976,796 A    11/1999    Szalay et al.

FOREIGN PATENT DOCUMENTS

WO    2004/058973 A1    7/2004

OTHER PUBLICATIONS

Watson et al., Recombinant DNA, Second Edition, 2001. pp. 153-154.*

"COP-Green expression vectors", [on line], EVRON Corp., Apr. 18, 2003, Internet<URL:http://wb.archive.org/web/2003041860445/http://www.evrogen.com/p-copGFP.shtml>.
Internet Archive wayback machine, "Searched for http://www.evrogen.com/p-copGFP.shtml", [on line], Internet: <URL:http://web.archive.org/web/*http://www.evrogen.com/p-copGFP.shtml>, 2003.
P.J. Herring, "Copepod luminescence", Hydrobiologia. (1998), vol. 167/168, pp. 183-195.
E.L. Markhaseva et al., "Calanoid copepods of the family *Aetideidae* of the World Ocean", Trudy Zool. Inst., (1996), vol. 268, pp. 1-10.
D.A. Shagin et al., "GFP-like Protein as Ubiquitous Metazoan Superfamily: Evolution of Functional Features and Structural Complexity", Mol. Biol. Evol., (2004), vol. 21, No. 5, pp. 841-850.
Bradford-Grieve, J.M., "A new species of *Benthopelagic calanoidcopepod* of the genus *Bradidius giesbrecht*, 1897 (*Calanoida: Aetideidae*) from New Zealand", New Zealand Journal of Marine Freshwater Research, (2003), vol. 37, No. 1, pp. 95-103.
Alvarez, M.P.J., "Two Bottom Living Copepoda *Calanoida aetideidae-Bradydius plinioi* and *Lutamator elegans* N. SP. Collected in Brazilian Waters", Bolm. Zool. (1984), vol. 8, pp. 93-106.
Markhaseva, E. L. et al., "Calanoid copepods of the family *Aetideidae* of the World Ocean", Trudy Zool. Inst. Ran., (1996), vol. 268, pp. 1-10, 68-86.
Markhaseva, E.L., *Calanoid copepods of the family Aetideidae of the world ocean*, Trudy Zool. Inst. Ran., (1996), vol. 268, pp. 108-129.
Masuda, et al., "A novel yellowish-green fluorescent protein from the marine copepod, *Chiridius poppei*, and its use as a reporter protein in HeLa cells", Gene: An international Journal on Genes and Genomes, May 10, 2006, pp. 18-25, vol. 372, Elsevier B.V., Amsterdam, NL.
STIC protein search titled "us-10-953-050-1.rag" pp. 1-9, May 2006.

* cited by examiner

*Primary Examiner* — Maria Leavitt
(74) *Attorney, Agent, or Firm* — Sughrue Mion, PLLC

(57) ABSTRACT

The present invention provides a novel fluorescent protein the wavelength of the maximum of the fluorescence of which exists in a wavelength side longer than 510 nm, and which exhibits yellow fluorescence or yellowish green fluorescence and can be expressed in a heterogeneous cell, and a gene encoding the same, wherein the fluorescent protein has an amino acid sequence as set forth in SEQ ID NO: 1 and it is a fluorescent protein derived from a copepod taxonomically classified to *Chiridius Poppei*.

4 Claims, 17 Drawing Sheets
(13 of 17 Drawing Sheet(s) Filed in Color)

Fig.1
(A) Under Day Light
(B) Under UV Light

Fig.6
in daylight
in UV light
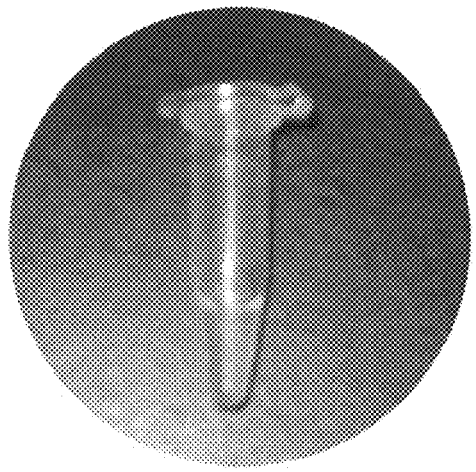
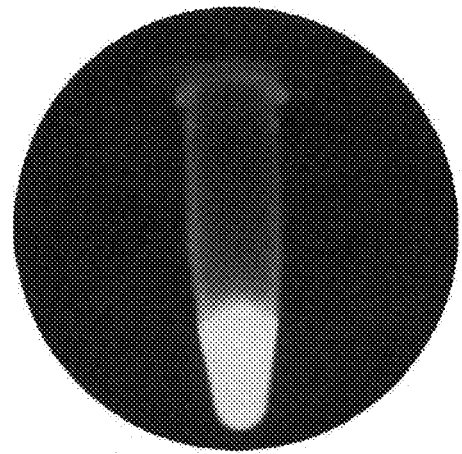

Fig.9

```
Cop-Green  M P A M K I E C R I T G T L N G V E F E L V G G G E G T P E
New FP     M T T F K I E S R I H G N L N G E K F E L V G G G - - V G E
           * . : : * * * . * * . * . * * *   * * * * * * * *     .   *

Cop-Green  Q G R M T N K M K S T K G A L T F S P Y L L S H V M G Y G F
NFP        E G R L E I E M K T K D K P L A F S P F L L S H C M G Y G F
           : * * *     : * * * . .   . * * * * * : * * * *   * * * * *

Cop-Green  Y H F G T Y P S G Y E N P F L H A I N N G G Y T N T R I E K
NFP        Y H F A S F P K G T K N I Y L H A A T N G G Y T N T R K E I
           * * * .   : : * . *   : *   : * * *     * * * * * * *   *

Cop-Green  Y E D G G V L H V S F S Y R Y E A G R V I G D F K V V G T G
NFP        Y E D G G I L E V N F R Y T Y E F N K I I G D V E C I G H G
           * * * * * : * . * . *   * *   . : : * * * .   :   * *

Cop-Green  F P E D S V I F T D K I I R S N A T V E H L H P M G D N V L
NFP        F P S Q S P I F K D T I V K S C P T V D L M L P M S G N I I
           * * . : *   * * . * . * : * *   . * * :   :   * * . . * : :

Cop-Green  V G S F A R T F S L R D G G Y Y S F V V D S H M H F K S A I
NFP        A S S Y A R A F Q L K D G S F Y T A E V K N N I D F K N P I
           . . * : * * : * . * : * * . : * :       *   . . : . * * . . *

Cop-Green  H P S I L Q N G G P M F A F R R V E E L H S N T E L G I V E
NFP        H E S F S K S G - P M F T H R R V E E T H T K E N L A M V E
           *   * :   : . *   * * * : . * * * * *   * : :   : * . : * *

Cop-Green  Y Q H A F K T P I A F A
NFP        Y Q Q V F N S A P R D M
           * * : . *   : : .
```

Expression in HeLa cell

Mammalian expression Vector

18hr After Transfection

FLUORESCENT PROTEIN AND GENE ENCODING THE SAME

CROSS-REFERENCE TO RELATED APPLICATIONS

This is a divisional of application Ser. No. 10/953,050 filed Sep. 30, 2004 (now U.S. Pat. No. 7,442,768), which is a Continuation-In-Part, under 35 U.S.C. §111(a) and 37 C.F.R. §1.53, of International Application No. PCT/JP2004/004818 filed Mar. 31, 2004. The entire disclosures of the prior applications, application Ser. Nos. 10/953,050 and PCT/JP2004/004818, are hereby incorporated by reference.

TECHNICAL FIELD

This invention relates to a novel fluorescent protein and a gene encoding the same. Specifically, the present invention relates to a novel fluorescent protein derived from a newly discovered sea plankton exhibiting luminescence ability and a coding gene which can be used for recombinant expression of the new fluorescent protein.

BACKGROUND ART

The green fluorescent protein (GFP: Green Fluorescent Protein) derived from a jellyfish, *Aequorea Victoria*, or a modified protein thereof is capable of recombinant expression in heterogeneous cells especially in various kinds of mammalian cells, and the obtained recombinant protein exhibits fluorescence performance in host cells. Using this feature, it has been attempted to use GFP derived from *A. victoria* and homologues thereof for various objects and applications as an in vivo fluorescent marker protein in the field of biochemistry, cell physiology and medicine (See Reference 1: Lippincott-Schwartz, J. G. H. Patterson, *Science* Vol. 300, 87-91 (2003); Reference 2: Tsien, R. Y., *Annu. Rev. Biochem.* Vol. 67, 509-544 (1998)).

In addition, besides GFP derived from *A. victoria*, GFP-like proteins have been cloned from class Hydrozoa of phylum Cnidaria (Cnidaria) and further GFP-like proteins have been also cloned from class Anthozoa of phylum Cnidaria.

Concerning these GFP-like proteins discovered in class Anthozoa of phylum Cnidaria, it is reported that they probably constitute a fluorescent protein family having bioevolutionarily the common origin (see Reference 3: Y. A. Labas et al., *Proc. Natl. Acad. Sci. U.S.A.* Vol. 99, 4256-4261 (2002)).

Concerning GFP derived from *A. victoria*, researches on the mechanism being essential to the exhibition of the fluorescence performance therein have progressed. First, it was revealed that in the process for folding into the natural steric structure, through which translated GFP polypeptide was converted into mature GFP having the fluorescence performance through the steps of cyclization of internal tripeptide site and subsequent oxidization thereto, which resulted in formation of a fluorophore. Furthermore, it has been also confirmed that SYG, 65-67$^{th}$ residues in the deduced amino acid sequence of wild type GFP derived from *A. victoria* is the internal tripeptide site, which forms a fluorophore. For example, it has been reported that a blue shift as compared with green fluorescence of wild type GFP is caused in the fluorescence in Y66H-GFP, in which mutation of Tyr to His at the 66$^{th}$ residue was made, showing blue fluorescence with a maximum at the wavelength of 448 nm. Furthermore, in S65T-GFP, where mutation of Ser to Thr at the 65$^{th}$ residue was made, the wavelength of a maximum of the fluorescence thereof was 510 nm, showing a slight red shift as compared with green fluorescence of wild type GFP. It has been also reported that formation of fluorophore, which was achieved through cyclization of an internal tripeptide: TYG site and subsequent oxidization, proceeds significantly more quickly in S65T-GFP than in SYG of wild type GFP.

Besides the aforementioned introduction of a mutation into the 65-67$^{th}$ SYG site, it has been also reported that when mutations of T203H, T203F and T203Y, which respectively replaces Thr with His, Phe, and Tyr at the 203$^{rd}$ position in the wild type GFP derived from *A. Victoria*, are introduced, the wavelength for the maximum in the fluorescence thereof shows a remarkable red shift to about 530 nm, resulting in yellow fluorescent protein (YFP: Yellow Fluorescent Protein). Moreover, it has been reported that EGFP ("enhanced" GFP), in which mutation of F64L replacing Phe with Leu at the 64$^{th}$ position adjacent to the 65-67$^{th}$ SYG site is made, exhibits a markedly improved maturation process accompanied by formation of fluorophore as compared with wild type GFP (see Reference 4: B. P. Cormack et al., *Gene* Vol. 173, 33-38 (1996)).

In this way, with regard to GFP-like proteins derived from various sea animals belonging to the phylum Cnidaria represented by GFP derived from *A. victoria*, a number of attempts utilizing them as an in vivo fluorescent marker protein, which can be expressed in an animal cell, have been made. In the meantime, it is known that there exist lots of marine organisms, especially animal planktons which show bioluminescence. Accordingly, the existence of novel fluorescent proteins is demanded which constitute another type of protein family having a bio-evolutionarily different origin from the fluorescent protein family to which GFP derived from *A. victoria* belongs. Thus, search for a new fluorescent protein family is desired, which can be used as an in vivo fluorescent marker protein which can be expressed in a host animal cell.

DISCLOSURE OF THE INVENTION

When a fluorescent protein is used as an in vivo fluorescent marker protein which can be expressed in a host cell, light excitation is performed from the outside of a host cell in order to observe the fluorescence. The wavelength used for this light excitation is selected from the light absorption band located at the shorter wavelength side (higher energy side) than the wavelength of the fluorescence emitted by the fluorescent protein. Fluorescence intensity obtained from a fluorescent protein depends on the product of the molar absorption coefficient ε (cm$^{-1}$·M$^{-1}$) at the excitation wavelength and fluorescence quantum yield η. Actually, excitation spectrum is measured by monitoring the fluorescence intensity obtained from the fluorescent protein, and the maximum peak wavelength therein is determined. For example, the excitation spectrum of GFP derived from *A. victoria* shows a main peak at 396 nm and a sub-peak at 475 nm. On the other hand, the maximum peak is shown at about 520 nm in the excitation spectrum of YFP obtained by modifying the GFP derived from *A. victoria*.

In the case that two types of in vivo fluorescent marker proteins are used in a host cell, such two types of fluorescent proteins different in fluorescence wavelength and excitation wavelength are thus needed. From this viewpoint, it is desired that a new fluorescent protein is provided, which emits distinguishable fluorescence when used in combination with a fluorescent protein which emits green fluorescence such as GFP derived from *A. victoria*. Specifically, it is desired that a new fluorescent protein is provided, of which the wavelength of the maximum of fluorescence is found at the longer wavelength side than the wavelength of the maximum of green fluorescence exhibited by GFP derived from *A. victoria* and the like and which has a bio-evolutionarily different origin from the fluorescent GFP-like protein family to which the GFP derived from *A. victoria* belongs.

The present invention is to solve the above-mentioned problems and the object of the present invention is to provide a new fluorescent protein which is derived from an animal plankton belonging to a phylum different from phylum Cnidaria, at least the wavelength of maximum of fluorescence of which exists at the longer wavelength side than 510 nm, exhibiting a yellow fluorescence or yellowish green fluorescence, and which is capable of recombinant expression in heterogeneous cells; and a gene encoding the same.

The present inventors searched for luminescent planktons that exhibit luminescence and fluorescence of a yellow or greenish yellow region from animal planktons inhabiting in the ocean in order to solve the above-mentioned problems. Specifically, a number of luminescent planktons were found out in the process of classification of animal planktons existing in the deep-sea water sampled from Toyama Bay in the Sea of Japan. Furthermore, animal planktons belonging to a phylum taxonomically different from the phylum Cnidaria and expressing a protein that shows yellow fluorescence or yellowish green fluorescence inside the body were sorted out from among said luminescent planktons. In the selection process, it was found that a kind of Red Copepoda, which is visible as red when visually observed under irradiation with white light among the planktons of the Crustacea, emitted a yellowish green fluorescence of high luminance under ultraviolet irradiation.

The present inventors tried to classify the Red Copepoda expressing a yellowish green fluorescent protein, which was discovered in said selection process, and found out that it belonged to phylum Arthropoda, subphylum Mandibulata, class Crustacea, subclass Coprpoda, and that the morphological features thereof agreed apparently with those of family Aetideidae, genus *Bradyidius*. At that stage, it was not established whether it is a species having been already reported or not. As a result of conducting taxonomical identification further based on a still more detailed comparison, it has been concluded that it belongs to *Chiridius poppei*.

Then, with regard to the yellowish green fluorescent protein of said Red Copepoda, identification of the nucleotide sequence of the gene encoding it and the determination of deduced amino acid sequence were tried. First, total RNAs were extracted from the Red Copepoda, the contained mRNAs were purified and reverse-transcriptase was used thereon to synthesize the corresponding cDNAs according to a conventional approach.

Taking into consideration that in many cases of the fluorescent GFP-like protein family to which the heretofore reported GFP derived from *A. victoria* belongs, the cloned cDNA is translated into a peptide chain in *E. coli* followed by folding of the translated peptide and formation of a luminophore and thereby expressed as a mature fluorescent protein, the present inventors inserted a synthesized cDNA into a general-purpose cloning vector: pBluescript II SK to construct a cDNA library, and examined whether the protein expression from cDNA occurred or not in *E. coli*. When the yellowish green fluorescent protein of interest expresses, the yellowish green fluorescence should be observed under irradiation with light of near-ultraviolet (wavelength range: 330 nm to 400 nm) or purple and indigo blue to bluish green color (wavelength range: 400 nm to 500 nm), and therefore, screening was made based on the existence of yellowish green fluorescence as a selection criteria. Consequently, one colony in which yellowish green fluorescence was clearly observed was selected, and succeedingly, secondary screening was performed for the selected colony to isolate the clones therefrom. The nucleotide sequence of the cDNA fragment inserted into the vector of the isolated clone was analyzed and the full-length amino acid sequence of the aimed yellowish green fluorescent protein derived from the Red Copepoda and the nucleotide sequence of the gene encoding the same were revealed. Furthermore, the present inventors compared the full-length amino acid sequence of said yellowish green fluorescent protein derived from the Red Copepoda with the full-length amino acid sequence of GFP derived from *A. victoria*, and confirmed that the similarity of these sequences is low, and therefore, it is a novel fluorescent protein having an origin bio-evolutionarily different from that of the fluorescent GFP-like protein family, and completed the present invention.

That is, the fluorescent protein derived from Copepoda according to the present invention is a fluorescent protein characterized that the protein is derived from a copepod taxonomically classified as *Chiridius poppei* and the full-length amino acid sequence of the fluorescent protein is:

```
MTTFKIESRI HGNLNGEKFE LVGGGVGEEG RLEIEMKTKD KPLAFSPFLL SHCMGYGFYH   60

FASFPKGTKN IYLHAATNGG YTNTRKEIYE DGGILEVNFR YTYEFNKIIG DVECIGHGFP  120

SQSPIFKDTI VKSCPTVDLM LPMSGNIIAS SYARAFQLKD GSFYTAEVKN NIDFKNPIHE  180

SFSKSGPMFT HRRVEETHTK ENLAMVEYQQ VFNSAPRDM                         219
```

(amino acid sequence listed in SEQ ID No: 1).

In addition, the gene encoding the fluorescent protein derived from Copepoda according to the present invention is a gene comprising the DNA encoding the amino acid sequence of SEQ ID No: 1. For example, it may be a gene characterized in that the nucleotide sequence of said DNA encoding of the amino acid sequence of SEQ ID No: 1 is as follows:

```
ATG ACA ACC TTC AAA ATC GAG TCC CGG ATC CAT GGC AAC CTC AAC GGG    48

GAG AAG TTC GAG TTG GTT GGA GGT GGA GTA GGT GAG GAG GGT CGC CTC    96

GAG ATT GAG ATG AAG ACT AAA GAT AAA CCA CTG GCA TTC TCT CCC TTC   144

CTG CTG TCC CAC TGC ATG GGT TAC GGG TTC TAC CAC TTC GCC AGC TTC   192
```

-continued

```
CCA AAG GGG ACT AAG AAC ATC TAT CTT CAT GCT GCA ACA AAC GGA GGT    240

TAC ACC AAC ACC AGG AAG GAG ATC TAT GAA GAC GGC GGC ATC TTG GAG    288

GTC AAC TTC CGT TAC ACT TAC GAG TTC AAC AAG ATC ATC GGT GAC GTC    336

GAG TGC ATT GGA CAT GGA TTC CCA AGT CAG AGT CCG ATC TTC AAG GAC    384

ACG ATC GTG AAG TCG TGT CCC ACG GTG GAC CTG ATG TTG CCG ATG TCC    432

GGG AAC ATC ATC GCC AGC TCC TAC GCT AGA GCC TTC CAA CTG AAG GAC    480

GGC TCT TTC TAC ACG GCA GAA GTC AAG AAC AAC ATA GAC TTC AAG AAT    528

CCA ATC CAC GAG TCC TTC TCG AAG TCG GGG CCC ATG TTC ACC CAC AGA    576

CGT GTC GAG GAG ACT CAC ACC AAG GAG AAC CTT GCC ATG GTG GAG TAC    624

CAG CAG GTT TTC AAC AGC GCC CCA AGA GAC ATG TAG                    660
```

(Nucleotide sequence listed in SEQ ID No: 2).

Moreover, the gene encoding of the fluorescent protein derived from Copepoda according to the present invention may be a cDNA characterized by being prepared from mRNA of the fluorescent protein derived from Copepoda and containing a coding region of the amino acid sequence shown in SEQ ID No: 1 and the nucleotide sequence of the cDNA is:

```
AGAACACTCA GTGTATCCAG TTTTCCGTCC TACTACAAAC                         40

ATG ACA ACC TTC AAA ATC GAG TCC CGG ATC CAT GGC AAC CTC AAC GGG    88

GAG AAG TTC GAG TTG GTT GGA GGT GGA GTA GGT GAG GAG GGT CGC CTC    136

GAG ATT GAG ATG AAG ACT AAA GAT AAA CCA CTG GCA TTC TCT CCC TTC    184

CTG CTG TCC CAC TGC ATG GGT TAC GGG TTC TAC CAC TTC GCC AGC TTC    232

CCA AAG GGG ACT AAG AAC ATC TAT CTT CAT GCT GCA ACA AAC GGA GGT    280

TAC ACC AAC ACC AGG AAG GAG ATC TAT GAA GAC GGC GGG ATC TTG GAG    328

GTC AAC TTC CGT TAC ACT TAC GAG TTC AAC AAG ATC ATC GGT GAC GTC    376

GAG TGC ATT GGA CAT GGA TTC CCA AGT CAG AGT CCG ATC TTC AAG GAC    424

ACG ATC GTG AAG TCG TGT CCC ACG GTG GAC CTG ATG TTG CCG ATG TCC    472

GGG AAC ATC ATC GCC AGC TCC TAC GCT AGA GCC TTC CAA CTG AAG GAC    520

GGG TCT TTC TAC ACG GCA GAA GTC AAG AAC AAC ATA GAC TTC AAG AAT    568

CCA ATC CAC GAG TCC TTC TCG AAG TCG GGG CCC ATG TTC ACC CAC AGA    616

CGT GTC GAG GAG ACT CAC ACC AAG GAG AAC CTT GCC ATG GTG GAG TAC    664

CAG CAG GTT TTC AAC AGC GCC CCA AGA GAC ATG TAG                    700

AATGTGGAAC GAAACCTTTT TTTCTGATTA CTTTCTCTGT TGACTCCACA             750

TTCGGAACTT GTATAAATAA GTTCAGTTTA AA                                782
```

(Nucleotide Sequence Listed in SEQ ID No: 3).

In addition, the present invention also provides an invention of a plasmid vector carrying said cDNA prepared from mRNA derived from Copepoda, that is, the plasmid vector according to the present invention is a plasmid vector pBluescriptII SK-NFP (FERM BP-08681), which is a plasmid vector being obtainable by inserting cDNA prepared from mRNA of the fluorescent protein derived from Copepoda and containing a coding region of the amino acid sequence shown in SEQ ID No: 1, wherein the nucleotide sequence of said cDNA is:

```
AGAACACTCA GTGTATCCAG TTTTCCGTCC TACTACAAAC                         40

ATG ACA ACC TTC AAA ATC GAG TCC CGG ATC CAT GGC AAC CTC AAC GGG    88

GAG AAG TTC GAG TTG GTT GGA GGT GGA GTA GGT GAG GAG GGT CGC CTC    136

GAG ATT GAG ATG AAG ACT AAA GAT AAA CCA CTG GCA TTC TCT CCC TTC    184
```

-continued

```
CTG CTG TCC CAC TGC ATG GGT TAC GGG TTC TAC CAC TTC GCC AGC TTC    232

CCA AAG GGG ACT AAG AAC ATC TAT CTT CAT GCT GCA ACA AAC GGA GGT    280

TAC ACC AAC ACC AGG AAG GAG ATC TAT GAA GAC GGC GGC ATC TTG GAG    328

GTC AAC TTC CGT TAC ACT TAC GAG TTC AAC AAG ATC ATC GGT GAC GTC    376

GAG TGC ATT GGA CAT GGA TTC CCA AGT CAG AGT CCG ATC TTC AAG GAC    424

ACG ATC GTG AAG TCG TGT CCC ACG GTG GAC CTG ATG TTG CCG ATG TCC    472

GGG AAC ATC ATC GCC AGC TCC TAC GCT AGA GCC TTC CAA CTG AAG GAC    520

GGC TCT TTC TAC ACG GCA GAA GTC AAG AAC AAC ATA GAC TTC AAG AAT    568

CCA ATC CAC GAG TCC TTC TCG AAG TCG GGG CCC ATG TTC ACC CAC AGA    616

CGT GTC GAG GAG ACT CAC ACC AAG GAG AAC CTT GCC ATG GTG GAG TAC    664

CAG CAG GTT TTC AAC AGC GCC CCA AGA GAC ATG TAG                    700

AATGTGGAAC GAAACCTTTT TTTCTGATTA CTTTCTCTGT TGACTCCACA             750

TTCGGAACTT GTATAAATAA GTTCAGTTTA AA                                782
```

(Nucleotide Sequence Shown in SEQ ID No: 3).

Furthermore, the present invention also provides an invention of use utilizing a gene encoding the fluorescent protein derived from Copepoda of the present invention for recombinant expression of the fluorescent protein derived from Copepoda in an in vitro culture system of mammalian cells, and the use of DNA having the nucleotide sequence shown in SEQ ID No: 2 according to the present invention is a use of DNA having the nucleotide sequence shown in SEQ ID No: 2 as a nucleotide sequence encoding the peptide chain shown in SEQ ID No: 1 in an in vitro culture system of mammalian cells for the purpose of allowing recombinant expression in said mammalian cells of the fluorescent protein derived from Copepoda which protein has the amino acid sequence shown in SEQ ID No: 1 as full-length amino acid sequence and using it as an in vivo fluorescent marker protein therein. For example, said mammalian cells may be a cell line derived from human which can be cultured in vitro.

BRIEF DESCRIPTION OF THE DRAWINGS

The patent or application file contains at least one drawings executed in color. Copies of this patent or patent application publication with color drawing(s) will be provided by the office upon request and payment of the appropriate fee.

FIG. 1 (a) shows the appearance of Red Copepoda microscopically observed under white light irradiation which Red Copepoda is the origin of the fluorescent protein of the present invention and FIG. 1 (b) shows regions emitting a yellowish green fluorescence which are in the organ inside the body of the Red Copepoda and fluorescence microscopically observed under irradiation with Dark Reader light (wavelength range: 420 nm to 500 nm);

FIG. 6 shows a visually observed result under white light irradiation and an observed result of yellowish green fluorescence under Dark Reader light (wavelength range: 420 nm to 500 nm) irradiation with the solution sample of the fluorescent protein derived from Red Copepoda which has a refining purity as shown in FIG. 5;

FIG. 9 shows a comparative alignment of the amino acid sequence between the fluorescent protein derived from Red Copepoda of the present invention (SEQ ID NO:1) and a fluorescent protein derived from Copepoda published by EVRΩGEN Company (SEQ ID NO:8);

BEST MODE FOR CARRYING OUT THE INVENTION

Figure 2:
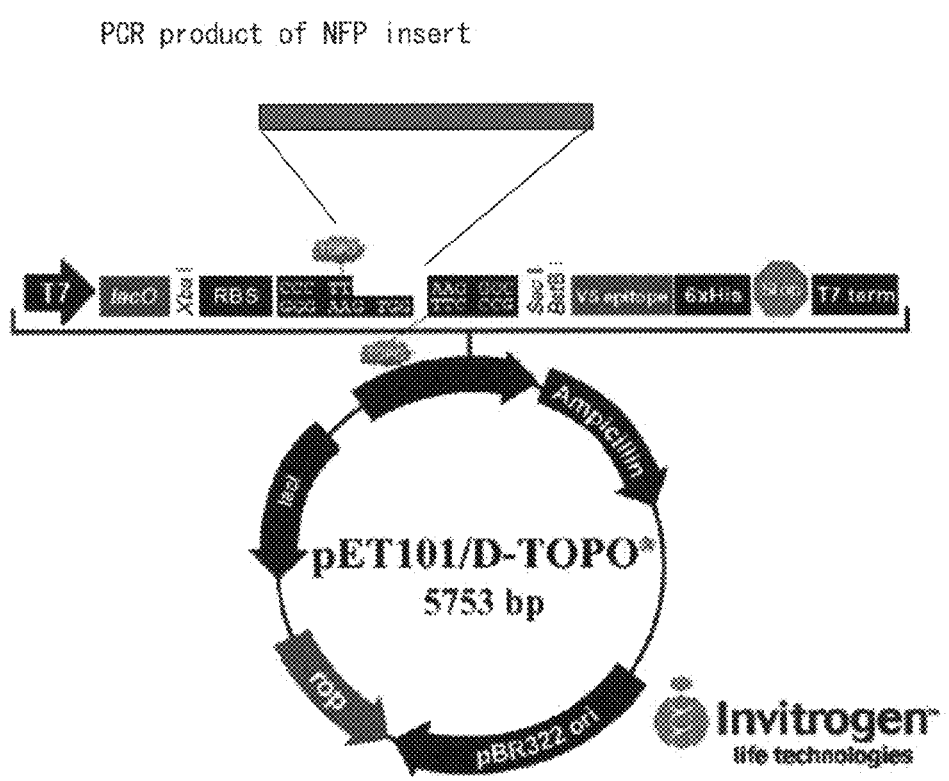
FIG. 2 is a drawing illustrating the composition of expression vector for the fluorescent protein derived from the Red Copepoda: pET101-NFP obtained by inserting the gene (673 bp) encoding the fluorescent protein of the present invention derived from the Red Copepoda into a commercially available plasmid pET101/D-TOPO (product of Invitrogen) (the cloning site sequence is set forth in SEQ ID NO:19)

The fluorescent protein derived from Copepoda of the present invention can be recombinant-expressed in a heterogenous host cell as a mature protein which has its natural fluorescence performance. In addition, the fluorescence of the recombinant-expressed fluorescent protein derived from Copepoda is a yellowish green fluorescence having a maximum at a wavelength of 518 nm and covering over a yellow zone (570 nm to 590 nm), and is distinguishable from a green fluorescence such as those by GFP derived from *A. victoria*. Therefore, they can be used as two types of in vivo fluorescent marker proteins in a host cell, which exhibit different fluorescences being distinctly separable from each other.

The fluorescent protein derived from Copepoda of the present invention is explained in more detail below.

First, the animal plankton which is the origin of the fluorescent protein of the present invention is a Crustacea plankton found in the deep-sea water sampled from Toyama Bay of the Sea of Japan at the depth of water of 321 m. As shown in FIG. 1 (*a*), it is a kind of Red Copepoda the appearance of which is visible as red when observed with a microscope under white light irradiation. It was taxonomically assumed that this Red Copepoda belonged to phylum Arthropoda, subphylum Mandibulata, class Crustacea, subclass Copepoda, and was possibly a species of family Aetideidae, genus *Bradyidius*, and as a result of taxonomical identification further based on a still more detailed comparison, it has been concluded that it belongs to *Chiridius poppei*. Moreover, when observed with a fluorescence microscope under irradiation with ultraviolet light (wavelength range: 420 nm to 500 nm), for example, Dark Reader light, regions emitting a yellowish green fluorescence are observed in the organ inside the body of the Red Copepoda as shown in FIG. 1 (*b*).

The present inventors investigated the regions emitting a yellowish green fluorescence observed inside the body of the Red Copepoda and as a result, it was concluded that they were not attributable to parasitism or adhesion of bacteria producing fluorescent protein but to the fluorescent protein derived from the Red Copepoda itself. Although such attempt that the planktons were collected to isolate the fluorescent protein therefrom was actually examined, it was judged that the amount of planktons available was insufficient, and it was difficult to collect a sufficient amount of the protein for the amino acid sequencing. Therefore, the present inventors judged that such approach that degenerate probes encoding a part of the amino acid sequence were prepared on basis of the result of amino acid sequencing to clone the gene of the fluorescent protein from genome DNA by means of the probe hybridizing method by was difficult to apply in this case.

Therefore, the present inventors tried screening of mRNA(s) which can be translated into the fluorescent protein among a variety of remaining mRNA(s) upon expression of the protein inside of the body the Red Copepoda. Specifically, a cDNA library was prepared from mRNA(s), and expression cloning method was applied using said cDNA library for the purpose of selecting out those capable of expressing a fluorescent protein.

First, total RNA was extracted using a commercially available RNA extraction reagent; TRIZOL reagent (product of Invitrogen) from the Red Copepoda, and subsequently, poly (A)+mRNA used for translation of various proteins was purified using a commercially available purification kit; Oligotex-dT30 <SUPER> mRNA Purification Kit (product of TAKARA). Furthermore, synthesis and amplification of corresponding cDNA from the purified mRNA was performed using a commercially available cDNA preparation kit: cDNA Synthesis kit (product of Stratagene). The prepared cDNAs were inserted into cloning vector: pBluescript II SK, and cDNA library was constructed.

Utilizing the portion derived from the nucleotide sequences of the primers for PCR amplification at both termini in the prepared cDNA, 5'-terminus of cDNA is made a Blunt end and 3'-terminus is made an edge digested by Xho I restriction enzyme. In the meantime, the Xho I restriction site in the multi-cloning site of a cloning vector: pBluescript II SK was enzymatically digested and the other terminus cleaved was made a Blunt end and the vector was ligated with the above-mentioned cDNA fragment so that the cDNA fragment was inserted into said site.

It has been revealed that in such a case of GFP derived from *A. victoria* reported up to now, expression from cDNA produced from mRNAs thereof is initiated within *E. coli*, and a peptide chain translated thereby is processed to result in a mature GFP. Similarly, vectors which constitute the prepared cDNA library derived from the Red Copepoda were introduced into *E. coli*, and then the inserted cDNAs were expressed to ascertain whether or not a protein exhibiting fluorescence was present among the proteins encoded thereby. One colony which emits fluorescence under irradiation with Dark Reader light (wavelength range: 420 nm to 500 nm) was found out under the condition of generating about 300,000 colonies. This one colony selected out in the primary screening, was subjected to a secondary screening on the same conditions and the clones were isolated.

The introduced vectors were collected from the isolated clone, and the nucleotide sequence of the inserted cDNA was determined. The sequencing was extended into cDNA inserted between Blunt-Xho I sites on basis of the known nucleotide sequence of the cloning vector pBluescript II SK used therefor. Consequently, as for a nucleotide sequence of the cDNA derived from the mRNA, which is used for expressing the fluorescent protein derived from the Red Copepoda in *E. coli*, sequence with full length of 782 bp and ORF (open reading frame) of 660 bp has been identified. The full-length nucleotide sequence (SEQ ID NO:3) and the amino acid sequence (SEQ ID NO:1) of 219 amino acids deduced from the ORF are shown below.

```
AGAACATCA GTGTATCCAG TTTTCCGTCC TACTACAAAC                                    40

ATG ACA ACC TTC AAA ATC GAG TCC CGG ATC CAT GGC AAC CTC AAC GGG              88
 M   T   T   F   K   I   E   S   R   I   H   G   N   L   N   G
 1               5                   10                  15

GAG AAG TTC GAG TTG GTT GGA GGT GGA GTA GGT GAG GAG GGT CGC CTC             136
 E   K   F   E   L   V   G   G   G   V   G   E   E   G   R   L
                 20                  25                  30

GAG ATT GAG ATG AAG ACT AAA GAT AAA CCA CTG GCA TTC TCT CCC TTC             184
 E   I   E   M   K   T   K   D   K   P   L   A   F   S   P   F
                 35                  40                  45

CTG CTG TCC CAC TGC ATG GGT TAC GGG TTC TAC CAC TTC GCC AGC TTC             232
 L   L   S   H   C   M   G   Y   G   F   Y   H   F   A   S   F
         50                  55                  60

CCA AAG GGG ACT AAG AAC ATC TAT CTT CAT GCT GCA ACA AAC GGA GGT             280
 P   K   G   T   K   N   I   Y   L   H   A   A   T   N   G   G
 65                  70                  75                  80

TAC ACC AAC ACC AGG AAG GAG ATC TAT GAA GAC GGC GGC ATC TTG GAG             328
 Y   T   N   T   R   K   E   I   Y   E   D   G   G   I   L   E
                     85                  90                  95

GTC AAC TTC CGT TAC ACT TAC GAG TTC AAC AAG ATC ATC GGT GAC GTC             386
 V   N   F   R   Y   T   Y   E   F   N   K   I   I   G   D   V
                 100                 105                 110

GAG TGC ATT GGA CAT GGA TTC CCA AGT CAG AGT CCG ATC TTC AAG GAC             424
 E   C   I   G   H   G   F   P   S   Q   S   P   I   F   K   D
             115                 120                 125

ACG ATC GTG AAG TCG TGT CCC ACG GTG GAC CTG ATG TTG CCG ATG TCC             472
 T   I   V   K   S   C   P   T   V   D   L   M   L   P   M   S
     130                 135                 140

GGG AAC ATC ATC GCC AGC TCC TAC GCT AGA GCC TTC CAA CTG AAG GAC             520
 G   N   I   I   A   S   S   Y   A   R   A   F   Q   L   K   D
145                 150                 155                 160

GGC TCT TTC TAC ACG GCA GAA GTC AAG AAC AAC ATA GAC TTC AAG AAT             568
 G   S   F   Y   T   A   E   V   K   N   N   I   D   F   K   N
                 165                 170                 175

CCA ATC CAC GAG TCC TTC TCG AAG TCG GGG CCC ATG TTC ACC CAC AGA             616
 P   I   H   E   S   F   S   K   S   G   P   M   F   T   H   R
                 180                 185                 190

CGT GTC GAG GAG ACT CAC ACC AAG GAG AAC CTT GCC ATG GTG GAG TAC             664
```

```
                              -continued
R   V   E   E   T   H   T   K   E   N   L   A   M   V   E   Y
        195                 200                 205

CAG CAG GTT TTC AAC AGC GCC CCA AGA GAC ATG TAG                 700
 Q   Q   V   F   N   S   A   P   R   D   M   *
        210                 215

AATGTGGAAC GAAACCTTTT TTTCTGATTA CTTTCTCTGT TGACTCCACA          750

TTCGGAACTT GTATAAATAA GTTCAGTTTA AA                             782
```

In addition, the present inventors prepared primers for PCR based on said nucleotide sequence, newly extracted total RNA from 31 individuals of Red Copepoda, performing RT-PCR using the RNA as a template, confirmed that amplification products having the corresponding nucleotide sequence and molecular weight, and the present inventors verified that it was indeed a gene encoding the fluorescent protein NFP (Namerikawa Fluorescent Protein) derived from the Red Copepoda.

In addition, based on the above-mentioned nucleotide sequence, as forward and reverse primers for PCR,

```
forward primer: pET-UP1 (28 mer)
5-CACCATGACAACCTTCAAAATCGAGTCC        (SEQ ID NO:
                                             4)

reverse primer: SalI-LP1 (35 mer);
5-CTCGTCGACCTACATGTCTCTTGGGGCGCTGTTGA (SEQ ID NO:
                                             5)
``` wherein in order to introduce a cleavage site for SalI restriction enzyme at the 3'-terminus thereof, a corresponding nucleotide sequence is appended thereto, were prepared and products of PCR amplification were obtained using as a template the vector collected from the isolated clone. As shown in FIG. 2, the 673 bp product of PCR amplification containing the ORF (open reading frame) therein was inserted into a commercially available plasmid pET101/D-TOPO (product of Invitrogen) to construct an expression vector pET101-NFP of the fluorescent protein NFP.

In the meantime, an expression vector of GST-tagged fluorescent protein: pGEX6P1-NFP was prepared in which the fluorescent protein derived from Red Copepoda was linked via a linker sequence containing a cleavage site for endopeptidase Factor Xa to the C-terminus of glutathion S-transferase (GST), a fusion partner. That is, utilizing as forward and reverse primers for PCR

```
    forward primer: GST-UP1 (43 mer)
                                          (SEQ ID NO: 6)
    5-CGAATTCATCGAAGGCCGCATGACAACCTTCAAAATCGAGTCC (SEQ ID NO: 4)
              5-CACCATGACAACCTTCAAAATCGAGTCC
``` wherein to the above-mentioned pET-UP1 (28 mer) were appended a partial sequence of ATCGAAGGCCGC (SEQ ID NO: 7) encoding the amino acid sequence for the cleavage site of protease Factor Xa and a corresponding nucleotide sequence GAATTC in order to introduce a cleavage site by EcoR I restriction enzyme at the 5'-terminus; and

Figure 3:
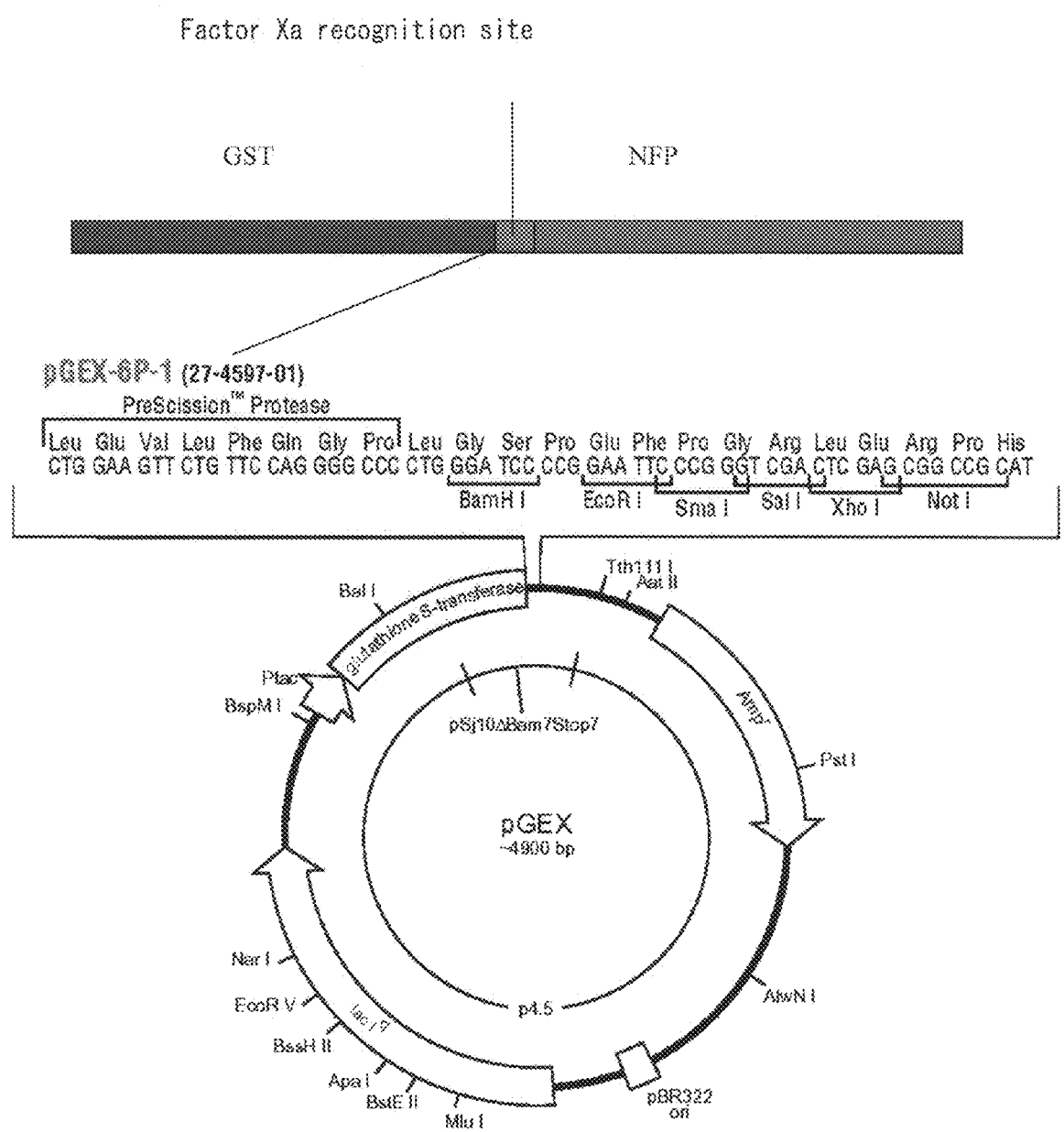
FIG. 3 illustrates the composition of expression vector for GST-tagged fluorescent protein: pGEX6P1-NFP obtained by inserting the gene (688 bp) encoding the fluorescent protein of the present invention derived from the Red Copepoda into a commercially available plasmid vector: pGEX-6P-1 (product of Amersham Biosciences) for the expression of fusion protein with a GST tag in which the fluorescent protein derived from Red Copepoda is connected to the C-terminus of glutathion S-transferase (GST) of a fusion partner, via a linker sequence containing a cleavage site for endopeptidase Factor Xa therein (SEQ ID NO:20 (amino acid sequence) and SEQ ID NO: 21 (nucleotide sequence))

```
reverse primer: SalI-LP1 (35 mer)
5-CTCGTCGACCTACATGTCTCTTGGGGCGCTGTTGA  (SEQ ID NO:
                                             5)
``` wherein in order to introduce a cleavage site for SalI restriction enzyme at the 3'-terminus thereof, a corresponding nucleotide sequence is appended thereto; products of PCR amplification were obtained by using as a template the vectors collected from the isolated clone. Once, the PCR amplification products were incorporated into pCR4 Blunt-TOPO (product of Invitrogen), and clone selection was performed using a selection marker. After each selected clone is cultured, plasmid: pCR4 Blunt-NFP contained was purified therefrom to check the molecular weight size and the nucleotide sequence of the DNA fragment inserted therein. Subsequently, as shown in FIG. 3, EcoR I/Sal I fragment of the insert DNA of 688 bp which contained ORF (open reading frame) was inserted into a commercially available plasmid vector: pGEX-6P-1 (product of Amersham Biosciences) for protein expression of the fusion type with a GST tag to construct an expression vector: pGEX6P1-NFP of the fluorescent protein NFP with a GST tag.

Figure 4:
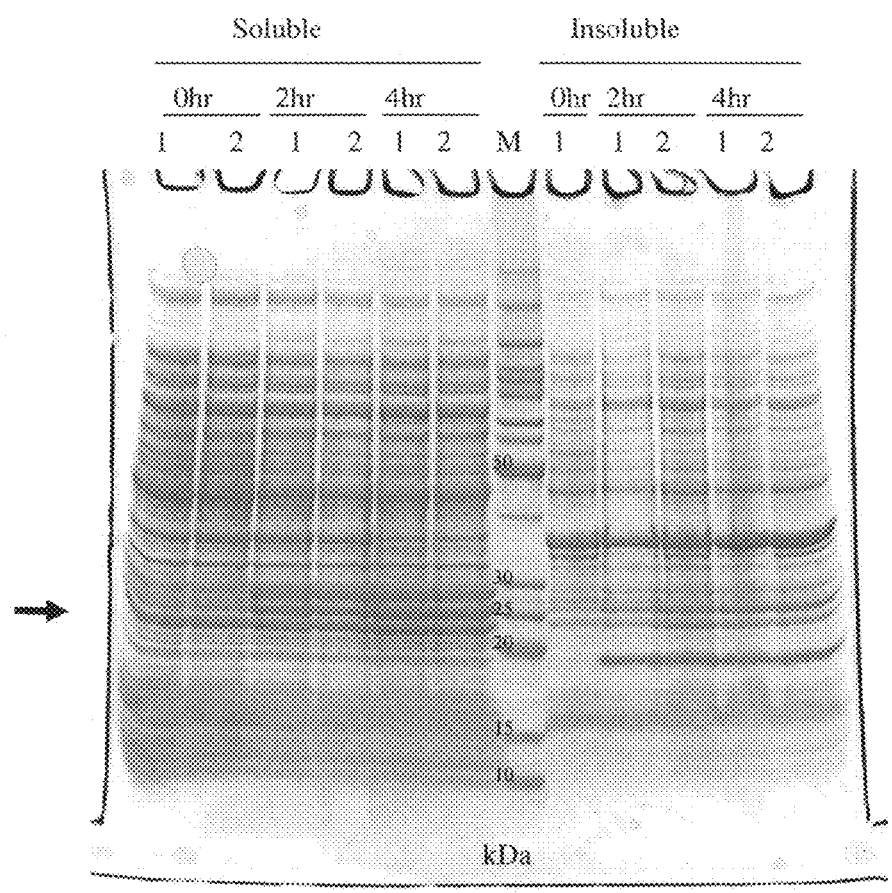
FIG. 4 shows the SDS-PAGE analysis results of the proteins included in soluble fractions (cytoplasmic components) and insoluble fractions (membrane ingredients), respectively, in the *E. coli* which has been transformed by expression vector: pBluescriptII SK-NFP of the fluorescent protein derived from Red Copepoda and indicates a new band of molecular weight 25 kDa found in the soluble fractions (cytoplasmic components) of the transformed *E. coli*.

E. coli was transformed using the expression vector: pET101-NFP of the fluorescent protein NFP shown in FIG. 2. Clone selection was carried out on the obtained transformed E. coli with use of an ampicillin resistance gene as a selection marker. Further, IPTG was employed to induce expression of the inserted gene through a promoter derived from the vector, and check was kept on expression of the fluorescent protein 2 hours and 4 hours after the induction. After IPTG-induced expression, the cultured cells of the transformed strain, in which expression of the fluorescent protein had been confirmed, was crushed, and then SDS-PAGE analysis was performed on the proteins contained in a soluble fraction (cytoplasmic components) and insoluble fraction (membrane components) which were separated by centrifugation (15,000 rpm; 18,800×g), respectively. Consequently, a new band of molecular weight 25 kDa was found in the soluble fraction (cytoplasmic components) of the transformed E. coli. That is, the molecular weight of the fluorescent protein derived from the Red Copepoda is predicted to be 24.7 kDa from the deduced amino acid sequence mentioned above, which is coincident with the new band of molecular weight 25 kDa shown in the results of SDS-PAGE analysis of FIG. 4.

Figure 5:
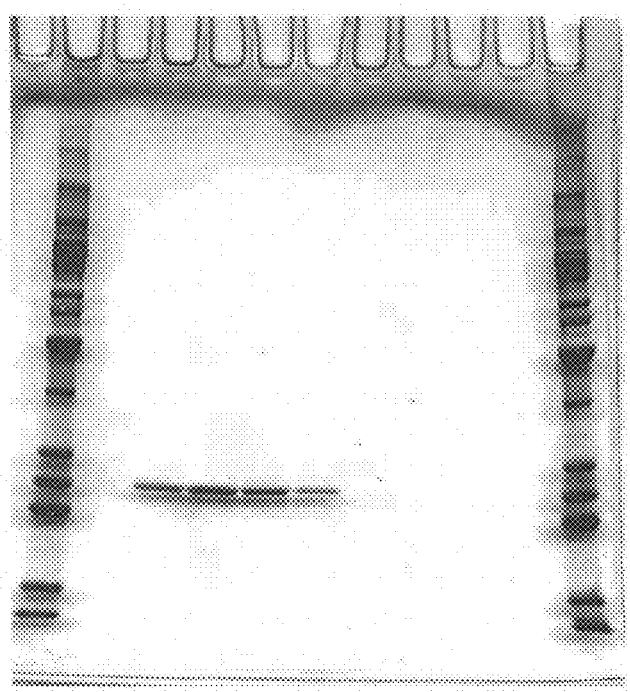
FIG. 5 shows the SDS-PAGE analysis results of the fluorescent protein recombinant purified and collected by anion exchange column: HiTrap DEAE FF (product of Amersham Biosciences) and gel filtration: HiLoad 16/60 Superdex 200 pg (product of Amersham Biosciences) from the soluble fraction (cytoplasmic components) of the mass culture of a transformed *E. coli* carrying expression vector: pET101-NFP of the fluorescent protein derived from Red Copepoda.
Figure 7:
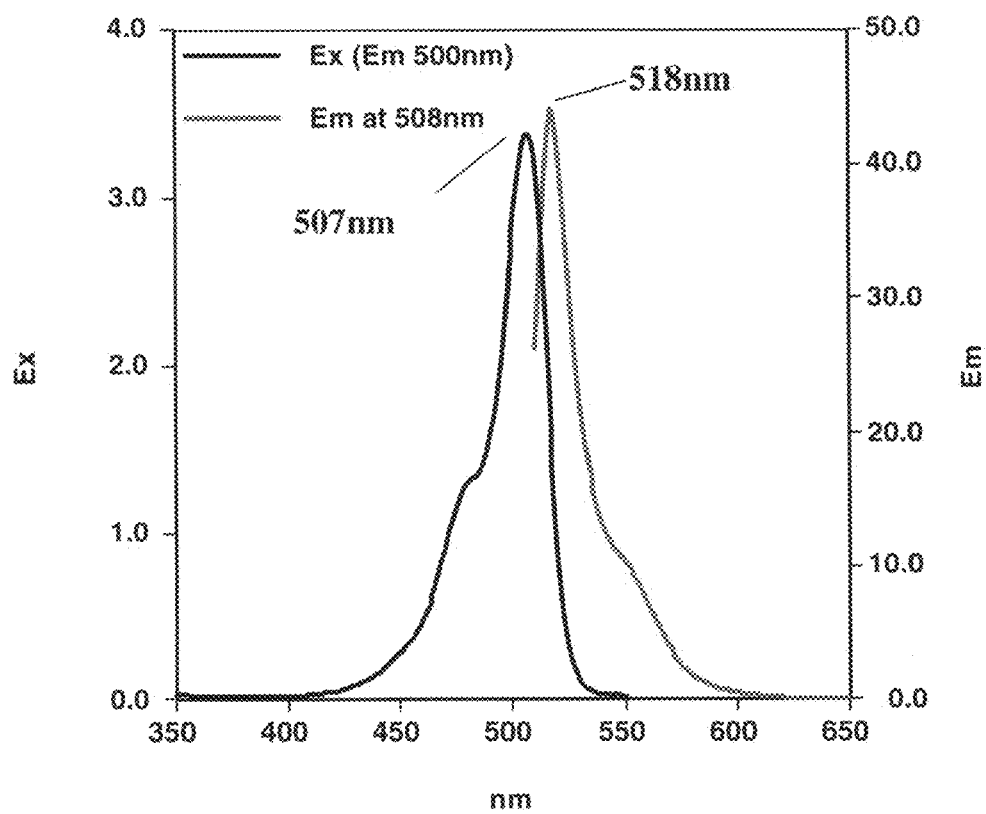
FIG. 7 shows the measurement results of the excitation spectrum measured by monitoring the fluorescence intensity at the wavelength of 500 nm, and the fluorescent spectrum measured by exciting at the wavelength of 508 nm for a solution sample of the fluorescent protein derived from Red Copepoda which has a refining purity as shown in FIG. 5.

The transformed E. coli carrying expression vector of the fluorescent protein derived from the Red Copepoda: pET101-NFP was subjected to large-scale culturing, and isolation and purification of the fluorescent protein recombinant was tried. The isoelectric point (pI) of the fluorescent protein recombinant was predicted (calculated) beforehand based on the deduced amino acid sequence thereof, and it was calculated as pI=6.50. With reference to the result, the soluble fraction (cytoplasmic components) was applied to an anion exchange column: HiTrap DEAE FF (product of Amersham Biosciences), and the fluorescent protein recombinant was collected in fractions with 4.8-8.8% B buffer under the following elution conditions:
A buffer: 20 mM Tris-HCl pH 7.6
B buffer: 1 M NaCl in A buffer;
linear gradient with B buffer of 0-20% (NaCl concentrations of 0 to 200 mM). Then the collected fractions were preliminarily concentrated by means of VIVASPIN20 under condition of MW 10,000 cut. This concentrated sample was applied to gel filtration: HiLoad 16/60 Superdex 200 pg (product of Amersham Biosciences), and the fluorescent protein recombinant was purified and collected as a fluorescent fraction having a molecular weight of 100 kDa or less under the elution condition: A buffer 20 mM Tris-HCl pH 7.6. SDS-PAGE analysis performed at this stage showed a state where the aimed fluorescent protein recombinant was almost purified as shown in FIG. 5. It is confirmed that the solution of purified protein sample at this stage emitted a yellowish green fluorescence under irradiation with Dark Reader light (wavelength range: 420 nm to 500 nm), as shown in FIG. 6. Of course, fluorescence is not observed in the control sample, which is prepared by subjecting a soluble fraction (cytoplasmic components) of host E. coli to the same purifying treatment. A fluorescence spectrum and an excitation spectrum was actually measured using the purified protein solution sample at this stage. The maximum peak was found at the wavelength of 507 nm in the excitation spectrum measured while monitoring the fluorescence intensity at the wavelength of 500 nm, as shown in FIG. 7. On the other hand, as for the fluorescence spectrum measured with excitation at the wavelength of 508 nm, a fluorescence having a maximum peak with a wavelength of 518 nm and covering over a yellow zone (wavelength range: 570 nm to 590 nm) was confirmed.

Figure 8:
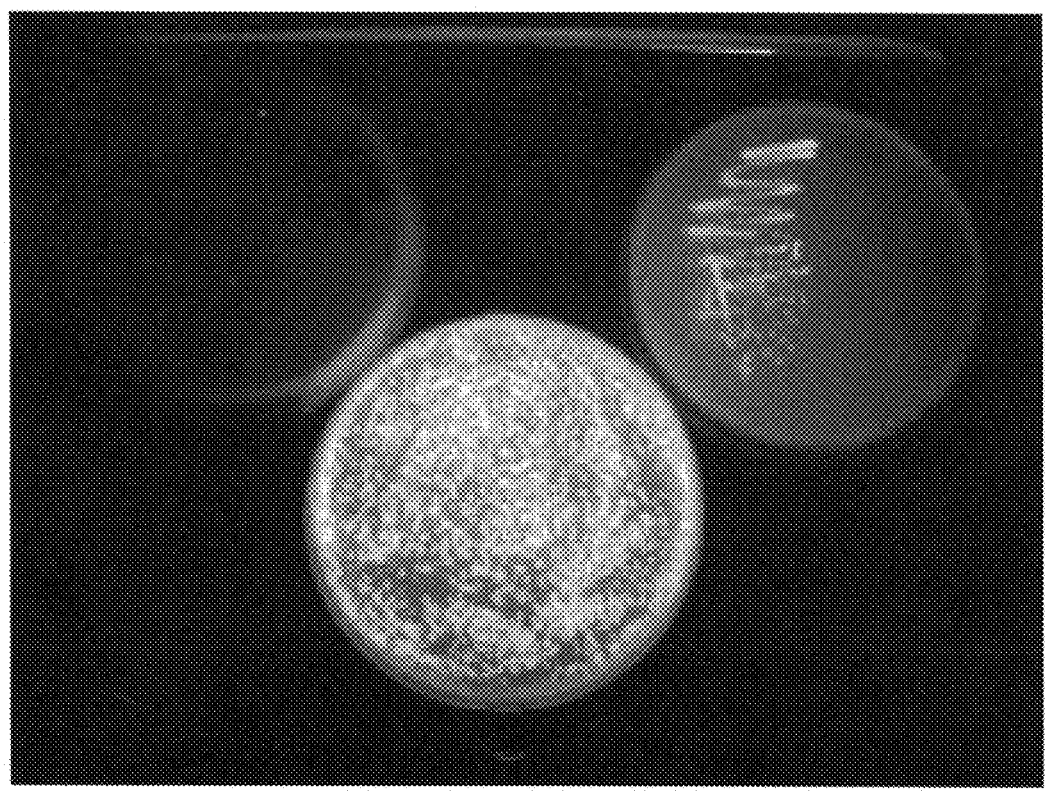
FIG. 8 shows the results observed under irradiation with Dark Reader light (wavelength range: 420 nm to 500 nm) for each colony formed on solid medium by culturing *E. coli* transformed by the expression vector for GST-tagged fluorescent protein: pGEX6P1-NFP (center); host *E. coli* as a negative control (upper left); and the isolated clone formed by inserting cDNA encoding the fluorescent protein derived from Red Copepoda into cloning vector: pBluescript II SK (positive control; upper right), respectively.

In addition, E. Coli was transformed using expression vector: pGEX6P1-NFP for the fluorescent protein with a GST tag shown in FIG. 3. The obtained transformed E. coli, host E. coli (negative control), and the isolated clone (positive control), in which cDNA encoding the fluorescent protein derived from the Red Copepoda was inserted into cloning vector: pBluescript II SK, were cultured on a culture medium, respectively. As shown in FIG. 8, when each colony was observed under irradiation with Dark Reader light (wavelength range: 420 nm to 500 nm), the colony of the obtained transformed E. coli emitted fluorescence, and it was confirmed that the fluorescent protein with a GST tag was expressed therein. Moreover, it is also confirmed that when recombinant expression thereof was made in the form of a fusion protein linked with another protein through a proper linker sequence, translated peptide chain is processed to form a mature fluorescent protein having a fluorescence performance through cyclization of the internal tripeptide site and its subsequent oxidization, which forms a fluorophore.

In the meantime, the present inventors searched for reports on the fluorescent protein derived from Copepoda other than the fluorescent protein derived from Red Copepoda of the present invention, and got sight of such information that a green fluorescent protein expression vector which include a coding region for humanized fluorescent protein gene derived from Copepoda has been marketed by EVRΩGEN Company quite recently under a trade name of Cop-Green™. The catalog for the product described that the recombinant expression product CopGFP of the fluorescent protein derived from Copepoda obtained from said commercially available green fluorescent protein expression vector, shows a green fluorescence exhibiting the maximum peak at the wavelength of 502 nm, and that the excitation spectrum thereof has a maximum peak at wavelength of 482 nm.

The amino acid sequence (SEQ ID NO:8) of the fluorescent protein derived from Copepoda coded in Cop-Green™ and its coding nucleotide sequence (SEQ ID NO:9) in which codons of ORF are replaced with corresponding humanized codons, which both have been published from EVRΩGEN Company, are shown below.

Sequence of the Humanized Version of the CopGFP's Open Reading Frame

```
ATG CCC GCC ATG AAG ATC GAG TGC CGC ATC ACC GGC ACC CTG AAC GGC    48
 M   P   A   M   K   I   E   C   R   I   T   G   T   L   N   G    16

GTG GAG TTC GAG CTG GTG GGC GGC GGA GAG GGC ACC CCC GAG CAG GGC    96
 V   E   F   E   L   V   G   G   G   E   G   T   P   E   Q   G    32

CGC ATG ACC AAC AAG ATG AAG AGC ACC AAG GGC GCC CTG ACC TTC AGC   144
 R   M   T   N   K   M   K   S   T   K   G   A   L   T   F   S    48

CCC TAC CTG CTG AGC CAC GTG ATG GGC TAC GGC TTC TAC CAC TTC GGC   192
 P   Y   L   L   S   H   V   M   G   Y   G   F   Y   H   F   G    64

ACC TAC CCC AGC GGC TAC GAG AAC CCC TTC CTG CAC GCC ATC AAC AAC   240
 T   Y   P   S   G   Y   E   N   P   F   L   H   A   I   N   N    80

GGC GGC TAC ACC AAC ACC CGC ATC GAG AAG TAC GAG GAC GGC GGC GTG   288
 G   G   Y   T   N   T   R   I   E   K   Y   E   D   G   G   V    96

CTG CAC GTG AGC TTC AGC TAC CGC TAC GAG GCC GGC CGC GTG ATC GGC   336
 L   H   V   S   F   S   Y   R   Y   E   A   G   R   V   I   G   112

GAC TTC AAG GTG GTG GGC AGC GGC TTC CCC GAG GAC AGC GTG ATC TTC   384
 D   F   K   V   V   G   T   G   F   P   E   D   S   V   I   F   128

ACC GAC AAG ATC ATC CGC AGC AAC GCC ACC GTG GAG CAC CTG CAC CCC   432
 T   D   K   I   I   R   S   N   A   T   V   E   H   L   H   P   144

ATG GGC GAT AAC GTG CTG GTG GGC AGC TTC GCC CGC ACC TTC AGC CTG   480
 M   G   D   N   V   L   V   G   S   F   A   R   T   F   S   L   160

CGC GAC GGC GGC TAC TAC AGC TTC GTG GTG GAC AGC CAC ATG CAC TTC   528
 R   D   G   G   Y   Y   S   F   V   V   D   S   H   M   H   F   176

AAG AGC GCC ATC CAC CCC AGC ATC CTG CAG AAC GGG GGC CCC ATG TTC   576
 K   S   A   I   H   P   S   I   L   Q   N   G   G   P   M   F   192

GCC TTC CGC CGC GTG GAG GAG CTG CAC AGC AAC ACC GAG CTG GGC ATC   624
 A   F   R   R   V   E   E   L   H   S   N   T   E   L   G   T   208
```

-continued

```
GTG GAG TAC CAG CAC GCC TTC AAG ACC CCG ATC GCA TTC GCC TGA      669
 V   E   Y   Q   H   A   F   K   T   P   I   A   F   A   *      223
```

When the amino acid sequence of the fluorescent protein derived from Red Copepoda of the present invention and this amino acid sequence of the fluorescent protein derived from Copepoda published from EVRΩGEN Company are aligned comparatively, considerably high homology is found including 112 identical amino acid residues and also homologous amino acid residues as is shown in FIG. 9. However, there exists a significant difference between the fluorescence spectra of the two.

The fluorescent proteins derived from these Crustacea show considerable homology, and it can be presumed that they constitute a family of new fluorescent protein. In addition, it is speculated that the tripeptide site, which may be involved in formation of the fluorophore, is a GYG site. Furthermore, it is presumed that the mature protein, in which cyclization and oxidization for the fluorophore has been finished up, shows similar steric structure in these two types of fluorescent protein derived from these Crustacea. It is shown that the recombinant expression product CopGFP of the fluorescent protein derived from Copepoda expressed from the expression vector marketed from EVRΩGEN Company shows fluorescence in the form of a monomer. When homology is taken into consideration, the fluorescent protein derived from Red Copepoda of the present invention can be also subjected to recombinant expression in a mammalian cell to be prepared in the form of a monomer, and it is expected to be usable as an in vivo fluorescent marker protein.

A cloning vector: pBluescriptII SK-NFP in which the gene (cDNA) encoding the fluorescent protein according to the present invention derived from Red Copepoda is inserted into the multi-cloning site of the cloning vector: pBluescript II SK was subjected to international deposition to International Patent Organism Depositary of National Institute of Advanced Industrial Science and Technology, (AIST Tsukuba Central 6, 1-1 Higashi 1-chome, Tsukuba, Ibaraki, 305-8566, Japan) under a deposit number FERM BP-08681 on March 31, Heisei 16 (2004) pursuant to the Budapest Treaty.

When the fluorescent protein derived from Red Copepoda according to the present invention is subjected to recombinant expression in a mammalian cell as an in vivo fluorescent marker protein, such a technique that an expression system for the GFP derived from *A. victoria* and the artificial modified variant thereof is employed to replace the coding region with said gene may be applicable. Similarly it is possible to subjected the fluorescent protein derived from Red Copepoda to recombinant expression not only in a mammalian cell but also in a host such as a bacteria, yeast, fungus and insect cell in which recombinant expression of the conventional GFP is possible. When the gene encoding the fluorescent protein derived from Red Copepoda is used in these recombinant expression systems, it is desirable to insert the gene into a expression vector after replacing the codons with the codons having high frequency of usage in the host, as required. Of course, variation is not introduced by such codon conversion into the amino acid sequence itself which is coded by the gene. Upon insertion to the expression vector, the coding gene in which codon conversion was carried out beforehand is digested by restriction enzyme in noncoding region of the both termini to be fragmented. In the case that a suitable restriction enzyme site as for the step of digesting with the restriction enzymes is not present therein, variation can be introduced by site-directed mutation method into the nucleotide sequences of said noncoding regions to create desired restriction enzyme site therein.

EXAMPLES

The present invention is explained particularly with reference to examples below. Although the examples shown herein are examples for best modes according to the present invention, scope of the present invention is not limited to these specific examples.
(Sampling of a Crustacea Plankton which Produces a Novel Fluorescent Protein)

The present inventors newly sampled the deep-sea water from off Toyama Bay of the Sea of Japan at the depth of water of 321 m and searched for an animal plankton which produces fluorescent protein for the purpose of discovering a new fluorescent protein family which does not have bioevolutionarily the common origin with GFP-like protein family derived from class Hydrozoa and class Anthozoa of phylum Cnidaria represented by a GFP derived from *A. victoria*.

It has been confirmed in the search process that a number of luminescent planktons exist in the deep-sea water sampled. Especially, those in which fluorescence resulted by fluorescent protein can be observed in the body organ and the fluorescence exhibits yellow fluorescence or yellowish green fluorescence were screened among the Crustacea planktons.

In the screening process, a kind of Red Copepoda the morphology of which is visible as red as shown in FIG. 1 (*a*) when observed with a microscope under white light irradiation was found to exhibit regions emitting yellowish green fluorescence in the organ inside the body of said Red Copepoda when observed with a fluorescence microscope under irradiation with ultraviolet (wavelength range: 420 nm to 500 nm), for example, Dark Reader light, as shown in FIG. 1 (*b*). It was taxonomically assumed that this Red Copepoda belonged to phylum Arthropoda, subphylum Mandibulata, class Crustacea, subclass Copepoda, and was possibly a species of family Aetideidae, genus *Bradyidius*. As a result of further conducting taxonomical identification in more detail, it has been concluded that it belongs to *Chiridius poppei*, which is classified into kingdom Metazoa (animal kingdom), phylum Arthropoda, subphylum Crustacea, class Maxillopoda, subcalss Copepoda, infraclass Neocopepoda, Gymnoplea, order Calanoida, family Aetideidae, genus *Chiridius*.
(Cloning of the Gene Encoding for the Fluorescent Protein NFP Derived from Red Copepoda)
Extraction of Total RNA From the sampled deep-sea water, about 300 individuals of collected Red Copepoda, after draining off water were suspended in 3 mL of TRIZOL reagent in total, and then frozen and stored at −80° C.

The Red Copepoda individuals stored by freezing was thawed at room temperature, and 3 mL of TRIZOL reagent was further added. The suspension was transferred to a 15 mL container made of Teflon for homogenizer, and was subjected to the crusher 10 times to crush the outer shell and the cells inside the body. The cell homogenize obtained were transferred to 15 mL falcon tube, and centrifuged (11,000 rpm) for 10 minutes at 2-8° C. The supernatant (first extraction fraction) was collected to another 15 mL falcon tube.

To the remaining precipitate pellet, 1 mL of TRIZOL reagent was added to form re-suspension. This re-suspension was transferred to a glass container for homogenizer, and subjected to homogenizing treatment again. After transferring the fluid treated again to another 15 mL falcon tube, 4 mL of TRIZOL reagent was added thereto, and it was centrifuged (11,000 rpm) for 10 minutes at 2-8° C. The resulted supernatant (second extraction fraction) was collected, and combined with the supernatant (first extraction fraction) of the preceding step to a total of 10 mL of the extract fraction, and 5 mL each thereof was dispensed to 15 mL falcon tubes.

0.2 mL of chloroform (1 mL per one tube) was added per 1 mL of TRIZOL reagent in a dispensed tube, sufficiently shaken to distribute the both liquid phases. After it is allowed to stand still for 2-3 minutes at room temperature, and centrifuged (11,000 rpm) for 10 minutes at 2-8° C. Separated aqueous phase (about 3 mL) was collected into another tube.

0.5 mL of isopropanol (2.4 mL per one tube), i.e., 1 mL per the originally added TRIZOL reagent, was added to the aqueous phase (about 3 mL) and mixed well. After the mixture was allowed to stand still for 5 minutes at room temperature, it was centrifuged (11,000 rpm) for 10 minutes at 2-8° C. After removing the supernatant, 5 mL of absolute ethanol was added to the alcohol precipitated fraction per one tube and stocked at −20° C.

To the ethanol precipitated pellet in the tube, 1 mL of 75% ethanol (5 mL per one tube), i.e., 1 mL per the originally added TRIZOL reagent was added, the mixture was vortexed, dispersed and mixed. The dispersion mixture was centrifuged (11,000 rpm) for 10 minutes at 2-8° C. After removing the supernatant, RNA precipitated pellet was allowed to stand still for 10 minutes at room temperature to evaporate the remaining solvent and dried up. One of the two total RNA samples dried up, which were purified from each of two dispensed samples, was stocked at −80° C. under dry state.

The other total RNA sample remained was mixed with 400 μL of water free from contamination of RNase and was allowed to stand still for 10 to 20 minutes and re-dissolved. A part of the solution was sampled and absorbance at the wavelengths of 260 nm: $OD_{260}$, at 280 nm: $OD_{280}$ and at 320 nm: $OD_{320}$ (background absorption) were measured. Based on the results, the concentration of RNA content was calculated from the absorbance $OD_{260}$ according to a conventional method. In addition, gel electrophoresis was performed under non-denaturing condition to analyze whether or not impurities were present therein, from which the purity of RNA contained was confirmed. The evaluation results of the concentration of RNA content as for the obtained total RNA sample are shown in Table 1.

To 200 μL of said total RNA solution, 200 μL of hybridization buffer: 2× Binding buffer attached to the kit was added and 400 μL of the solution in total was homogenized. 20 μL of a dispersion of Oligotex-dT30 was added to this RNA solution and mixed well. The solution in the tube was heated up to 70° C., held for 3 minutes, and succeedingly, it was allowed to be cooled down to room temperature for 10 minutes to perform hybridization of the Oligo-dT probe part of Oligotex-dT30 to the poly (A) tail of poly(A)+mRNA and. Centrifugation (15,000 rpm) was performed for 5 minutes and Oligotex-dT30 was separated as a precipitation fraction. Supernatant including the RNA component which has not hybridized with Oligotex-dT30 was removed.

The precipitation fraction was dispersed in 350 μL of washing buffer attached to the kit, and the precipitation fraction was transferred to a tube for centrifugal column. Centrifugation (15,000 rpm) was performed for 30 seconds and the supernatant resulted was removed. The same washing procedure was further performed using the same amount of washing buffer.

50 μL of DEPC-water (aqueous solution) attached to the kit heated to 70° C. beforehand was added to the precipitation fraction washed twice and this mixture was transferred to another tube for centrifugal column. Centrifugation (15,000 rpm) was performed for 30 seconds and the supernatant including poly(A)+mRNA detached from the probe of Oligotex-dT30 was collected. 50 μL of DEPC-water (aqueous solution) heated to 70° C. beforehand was added again to the precipitation fraction, the same procedure for detaching from the probe was repeated, and the supernatant was collected. The collected supernatants were pooled to form a solution containing purified mRNA in a total amount of 100 μL.

To this solution containing purified mRNA, 10 μL of 3 M of sodium acetate aqueous solution and 100 μL of 100% isopropanol were added and mixed well. Then, the mixture was allowed to stand still for 10 minutes at −20° C. and mRNA contained therein was subjected to alcohol precipitation. Centrifugation (14,000 rpm) was performed for 30 minutes, and mRNA precipitated was brought together in a precipitation fraction, and the supernatant was removed. Furthermore, 1 mL of 75% ethanol was added to the precipitation fraction of deposited mRNA, and mixed well. Centrifugation (14,000 rpm) was performed for 5 minutes, the precipitation fraction of mRNA precipitated was separated, and the supernatant was removed.

The purified mRNA precipitation obtained was re-dissolved into 11 μL of DEPC-water (aqueous solution). A part of it was taken as a sample for evaluation, and remaining purified mRNA sample solution (10.5 μL) was frozen and

TABLE 1

| Sample | $OD_{260}$ | $OD_{280}$ | $OD_{320}$ | Dilution Ratio | RNA concentration μg/μL | Total Volume μL | Amount of RNA μg | $OD_{260}/OD_{280}$ |
|---|---|---|---|---|---|---|---|---|
| Red Copepoda | 0.29 | 0.16 | 0.001 | ×100 | 1.14 | 400 | 456 | 1.75 |

Purification of Poly(A)+mRNA

Poly(A)+mRNA contained was separated and purified from 200 μL of the purified total RNA solution (concentration of RNA content 1.14 μg/μL) prepared above by means of a commercially available purification kit; Oligotex-dT30<SUPER> mRNA Purification Kit (product of TAKARA).

stored at −80° C. In addition, concentration of RNA content was evaluated using the sample for evaluation. Gel electrophoresis was also performed for the supernatant removed and the purified mRNA precipitation under non-denaturing condition at each stage of the purification process to verify progress step in purification. The evaluation results of the concentration of RNA content for the purified mRNA sample obtained thereby are shown in Table 2.

TABLE 2

| Sample | $OD_{260}$ | $OD_{280}$ | $OD_{320}$ | Dilution Ratio | RNA concentration μg/μL | Total Volume μL | Amount of RNA μg | $OD_{260}/OD_{280}$ |
|---|---|---|---|---|---|---|---|---|
| Red Copepoda | 0.10 | 0.055 | 0.011 | ×200 | 0.672 | 10.5 | 7.06 | 1.91 |

Synthesis of cDNA Using mRNA as a Template

The purified mRNA was used as a template to synthesize cDNA thereof by means of a commercially available cDNA synthesis kit: cDNA Synthesis Kit (Stratagene).

First, single stranded cDNA (first strand) was synthesized according to the following procedures.

To a solution of mixture of 5 μL of a buffer for reverse transcription: 10×1$^{st}$ strand buffer, 3 L of methyl dNTP mixture, 2 μL of linker-primer mixture solution, 1 μL of RNase Block Ribonuclease Inhibitor Solution attached to the kit and 30.06 μL of water (RNase free) was added 7.44 μL (amount of mRNA: 5 μg) of a purified mRNA solution which has been once heat-treated at 70° C. for 3 minutes to eliminate the high order structure and rapidly cooled down by ice, and they are mixed gently. The mixture was held at room temperature for 10 minutes and a primer was hybridized on the 3'-terminus of mRNA. 1.5 μL of a solution of reverse transcriptase: Strata-Script Riverese Transcriptase attached to the kit was added and gently mixed and enzyme reaction was performed at 42° C. for one hour.

Subsequently, the complementary strand (second strand) was synthesized according to the following procedures by using the synthesized single stranded cDNA (first strand) as a template.

To 50 μL of the obtained solution of the enzyme reaction under ice cooling were added 20 μL of DNA synthesis buffer: 10×2$^{nd}$ strand buffer for DNA synthesis attached to the kit, 6 μL of 2$^{nd}$ strand dNTP mixture and 111 μL of distilled water (DDW), successively, and further 2 μL of RNaseH solution (enzyme concentration 1.5 U/μL) as ribonuclease and 11 μL of DNA pol.I solution (enzyme concentration 9.0 U/μL) as a DNA polymerase, and mixed gently. Remaining mRNA is decomposed by RNaseH and, while of the synthesis of the complementary strand (second strand) was advanced by DNA pol.I from the upstream primer by using the prepared single stranded cDNA (first strand) as a template. After the solution of the enzyme reaction was held at 16° C. for 2.5 hours to extend the complementary strand (second strand) to result in double strand cDNA, it was ice-cooled and the enzyme reaction was stopped.

Blunting of the Termini of the Double Strand cDNA

Both the termini of said double strand cDNA were treated to convert into a blunt end according to the following procedures.

To the reaction solution containing the above-mentioned double strand cDNA, 23 μL of a blunting dNTP mixture and 2 μL of a cPfu enzyme solution (enzyme concentration 2.5 U/μL) were added. After the reaction solution was vortexed and mixed uniformly, it was held at 72° C. for 30 minutes, and enzyme processing was carried out.

After 30 minutes, 200 L of phenol was added to the reaction solution, and the mixture was vortexed to mix up. Centrifugation (15,000 rpm) was performed for 2 minutes to separate a liquid phase, and the upper aqueous layer was collected. To the aqueous layer collected, 200 μL of chloroform was added, and it was vortexed to mix up. Centrifugation (15,000 rpm) was performed for 2 minutes to separate a liquid phase, and the upper aqueous layer was collected.

To the aqueous layer collected, 20 μL of 3 M sodium acetate aqueous solution and 400 μL of anhydrous ethanol were added and the mixture was mixed well by vortexing and the cDNA contained therein was ethanol precipitated. Centrifugation (15,000 rpm) was performed for 60 minutes to separate cDNA precipitation into a precipitation fraction. The supernatant was removed, 500 μL of 70% ethanol was added to the remaining precipitation fraction of the cDNA separation, and mixed well. Centrifugation (15,000 rpm) was performed for 2 minutes, and again, the cDNA precipitation was separated into a precipitation fraction, and the supernatant was removed. The pellet of the collected cDNA separation was dried up.

The dried pellet of the cDNA separation was held in 9 μL of EcoRI adapter solution at 4° C. for one hour and re-dispersed. To this solution, 4.5 μL of commercially available Ligation reaction solution: Ligation High was added, the mixture was held at 16° C. overnight (16 hours), and Eco RI adapter was linked to the cDNA terminus. To the reaction solution, 186.5 μL of distilled water was added to dilute it to total 200 μL. Furthermore, 200 μL of phenol was added and it was mixed well by vortexing. Centrifugation (15,000 rpm) was performed for 5 minutes to separate liquid phase, and upper aqueous layer was collected. To the aqueous layer collected, 200 μL of chloroform was added and centrifugation (15,000 rpm) was performed for 5 minutes to separate liquid phase, and the upper aqueous layer was collected.

To the aqueous layer collected, 10 μL of 3 M of sodium acetate aqueous solution and 200 μL of 100% isopropanol were added and it was mixed well by vortexing to alcohol precipitate the cDNA contained. cDNA precipitation was subjected to centrifugation (15,000 rpm) at 4° C. for 60 minutes, and separated into a precipitation fraction. The supernatant was removed, 500 μL of 70% ethanol was added to the remaining precipitation fraction of the cDNA separation, and mixed well. cDNA separation was subjected to centrifugation (15,000 rpm) for 2 minutes, separated into a precipitation fraction, and the supernatant was removed. The pellet of the collected cDNA separation was dried up.

The pellet of the collected cDNA separation was re-dispersed well in a mixed solution of 20 μL of distilled water, 3 μL of T4 PNK buffer, 3 μL of 509 glycerol and 3 μL of 75 mM ATP solution. This reaction solution for T4 PNK enzyme was cooled down at −20° C. After thawing the enzyme solution, 1 μL of T4 Polynucleotide Kinase solution of a commercially available enzyme solution set (product of TAKARA) was added, and at 37° C. held for 1 hour to perform the enzymatic reaction. After completing phosphorylation to 5'-terminus of the double strand cDNA, heating was maintained at 70° C. for 30 minutes to perform heat-denaturation treatment, and the reaction was ended.

Treatment for Xho I Digestion of the Double Strand cDNA

The double strand cDNA treated to convert into a blunt end was subjected to Xho I digestion according to the following procedures.

30 µL of said double strand cDNA treated to convert into a blunt end, 11.5 µL of commercially available buffer solution (product of TAKARA): 10×H Buffer 11.5 µL for a restriction enzyme reaction, 70.5 µL of water (DDW), 3 µL of Xho I restriction enzyme solution (enzyme concentration 10 U/muL) of a commercially available restriction enzyme solution kit (product of TAKARA) were mixed to prepare a 115 µL in total of the reaction solution. After performing enzyme digestion at 37° C. for 2 hours, 200 µL of phenol was added, and it was mixed well by vortexing. Centrifugation (15,000 rpm) was performed for 5 minutes, and liquid layer was separated and the upper aqueous layer was collected. To the aqueous layer collected, 115 µL of chloroform was added, and it was mixed by vortexing. Centrifugation (15,000 rpm) was performed for minutes, and liquid layer was separated and the upper aqueous layer was collected.

Subsequently, 115 µL of the collected aqueous layer containing cDNA fragments enzymatically digested was applied to S-300 spin column which has been equilibrated by adding 3 times volume of 1×STE buffer. Centrifugation (1,500 rpm; 400×g) was performed for 2 minutes, and 105 µL of separated aqueous layer was collected. 200 µL of absolute ethanol was added to the collected aqueous layer and was allowed to stand still at −20° C. for 1 hour to precipitate cDNA fragments. Centrifugation (15,000 rpm) was carried out for 60 minutes at 4° C. to separate the cDNA fragment precipitation into a precipitation fraction. Washing procedure, in which the precipitation fraction of the cDNA separation was washed by adding 900 µL of 70% ethanol thereto, was repeated twice, and then the collected pellet of cDNA fragments precipitation was dried.

The collected pellet of cDNA fragments separation was re-dispersed in 6.0 µL of TE buffer to obtain a solution thereof. A part of the solution (1.0 µL) was sampled and the concentration of the cDNA contained therein was evaluated. The concentration of cDNA was 404.1 ng/µL, and 5.0 µL in total of a solution of double strand cDNA fragments was obtained which had a Blunt end at 5'-terminus and Xho I digest-treated end at 3'-terminus.

Formation of the Insertion Site with Blunt-End/Xho I Cleavage into the Multi-Cloning Sites of Cloning Vector: pBluescript II SK A commercially available vector: pBluescript II SK (+) (product of Stratagene) was proliferated beforehand to prepare a solution (concentration 500 ng/µL) of pBluescript II SK (+). 30 µL in total of a reaction solution being composed of 6 µL of the vector solution (amount of vector: 3 µg), 3 µL of 10×H Buffer, 1 µL of Xho I restriction enzyme solution (enzyme concentration 10 U/µL) and 20 µL of water (DDW) was held at 37° C. for 3 hours, and the vector was enzymatically digested at Xho I site. The main fragment of the enzymatically digested vector was separated and purified by MinElute method, and collected as 26 µL of eluate in Elution Buffer.

To 26 µL of the eluate, 3 µL of CIAP buffer (One-phor-All buffer) and 1 µL of CIAP Enzyme solution were added, and 30 µL in total of the reaction solution obtained was held at 37° C. for 30 minutes, and CIAP processing was performed only to the Xho I site. The main fragment of the vector treated was separated and purified by MinElute method, and collected as 26 µL of eluate in Elution Buffer.

To 26 µL of the eluate, 3 L of 10×H Buffer and 1 µL (enzyme concentration: 15 U/µL) of Eco RV restriction enzyme solution were added, and the mixture was held at 37° C. overnight (14 hours), and one side of the Xho I cleavage end of the vector was subjected to processing by Eco RV. As a result, vector: pBluescript II SK (+) was processed to yield a severed fragment having an insertion site with Blunt-end/Xho I cleavage site.

The reaction solution after the above-mentioned Eco RV processing was subjected to 0.76 agarose gel electrophoresis, and a band of the DNA fragment which has the target size was excised. The gel cut out was processed by Ultra free DA, and centrifugation (7,000 rpm) was performed for 10 minutes to collect a liquid layer containing the vector DNA fragments. Subsequently, the vector DNA fragments were separated and purified by MinElute method, and collected as 20 µL of eluate in Elution Buffer. The DNA fragment contained in the vector DNA fragment solution was once precipitated with ethanol and then re-dispersed in 5 µL of Elution Buffer to prepare 94.5 ng/µL of the vector DNA fragment solution.

Construction of cDNA Library

The fragments of vector pBluescript II SK (+) in which said insertion site of the Blunt-end/Xho I cleavage site was formed and double strand cDNA fragments having a Blunt end as 5'-terminus and Xho I digest-treated end at 3'-terminus were ligated to construct cDNA library.

0.53 µL of vector DNA fragment solution (DNA amount: 50 ng), 1 µL pf a solution of double strand cDNA fragments having such processed termini (DNA amount: 200 ng) and 0.765 µL of Ligation High were mixed, held at 16° C. overnight (14 hours) to attempt to ligate both the DNA fragments. The obtained plasmid vectors contained cDNA inserted therein, which were prepared from mRNAs collected from Red Copepoda, and thus cDNA library was constructed.

Introduction of a Plasmid Vector to Host E. coli

The constructed cDNA library was introduced to host E. coli by electroporation method, and the transformed strain was selected. Introduction of a plasmid vector to the host E. coli by electroporation method was carried out according to the following procedures.

To 2.295 µL of Ligation solution containing the cDNA library constructed, 5 µL of Strata Clean Resin solution was added, and mixed well by vortexing for 15 seconds. The Resin was settled by centrifugation, and the supernatant was collected into another tube. 5 µL of the Resin solution was added again to the supernatant and mixed well by vortexing for 15 seconds. The Resin was settled again by centrifugation, and the supernatant was collected into another tube.

Each 2.5 µL of water (DDW) was added to the Resin sediments remaining in the two tubes respectively and washed. The Resin was settled by centrifugation, liquid layer containing the plasmid vector collected by washing was separated.

The previous supernatants and the collected liquid layer were pooled to obtain a solution containing the plasmid vector of 10 µL in total. Centrifugation of this mixed solution was performed and the Resin slightly left therein was made to sediment once again, and the supernatant was collected into another tube. Enzyme used for the Ligation reaction is removed from the collected supernatant and a plasmid DNA solution was obtained.

As for TOP10 and TenBlue strains used as host E. coli, frozen competent cells stored were thawed at ice temperature. 5 µL of the plasmid DNA solution subjected to Resin adsorption processing was added to 40 µL of a competent cell suspension thawed of the host E. coli. A commercially available electroporation equipment: E. coli Pulser (product of Bio-rad) was used for electroporation injection to host cells in 0.1 mm gap cuvette at 1.7 kV of pulse voltage. The time constant of the pulse used is set to 4.1 µs for the system of cDNA library/TOP10 strain and 4.0 µs for the system of cDNA library/TenBlue strain. After the treatment for vector injection, 955 µL of a culture medium component SOC heated to 37° C. beforehand was added to 45 µL of the solution in which host E. coli was suspended, and the fluid was shaken to culture at 37° C. for 1.5 hours.

Then, 5 µL was sampled from 1000 µL of the obtained culture solution, 100 µL of the culture medium component SOC was added, and the mixture was inoculated on 9 cmϕ dish plate and cultured for two days at room temperature (20° C.). 428.57 µL of 50% glycerol was added to 995 µL of the remaining culture solution, and the mixed solution (at the final concentration of 15% glycerol content) was frozen and stocked at −80° C.

The number of colonies formed which show ampicillin resistance was counted on the plate culture, and they were 1425 colonies for the system of cDNA library/TOP10 strain and 700 colonies for the system of cDNA library/TenBlue strain. Therefore, density of the transformed strains contained in said culture solution is equivalent to $2.8 \times 10^5$ cfu/mL ($1.1 \times 10^7$ cfu/µg vector) for the system of cDNA library/TOP10 strain and $1.4 \times 10^5$ cfu/mL ($5.6 \times 10^6$ cfu/µg vector) for the system of cDNA library/TenBlue strain, respectively.

In the meantime, the ratio of the strains having a vector in which cDNA fragment was inserted among the transformed strains (cDNA library efficiency) was evaluated using the colony PCR method. Whether or not the vector contains cDNA fragment being inserted between T7 promoter site located upstream of the multi-cloning site of the vector pBluescript II SK (+) and T3 promoter site located downstream of said multi-cloning site was confirmed according to the following procedures.

The colony PCR was performed utilizing

```
T7 primer: GTAATACGACTCACTATAGGGC    (SEQ ID NO: 10)
``` which corresponds to the nucleotide sequence of T7 promoter site, as a forward primer and

```
           TTAATTGGGAGTGATTTCCC      (SEQ ID NO: 11)
3 primer:  AATTAACCCTCACTAAAGGG      (SEQ ID NO: 12)
``` which is complementary to the nucleotide sequence of T3 promoter site, as a reverse primer; and PCR amplification was performed by using as a template the vector DNA contained in a clone with use of a commercially available DNA polymerase: KOD Dash DNA polymerase. The temperature conditions and reaction solution composition used for the PCR reaction are summarized in Table 3.

TABLE 3

Temperature conditions of PCR reaction:
Used equipment: Mastercycler (eppendorf)

| Cycle operation | Temperature ° C. | Duration | |
|---|---|---|---|
| Denaturing | 96 | 1 min | |
| Annealing | 55 | 5 sec | |
| Extension | 74 | 2 min | 25 times |
| Denaturing | 96 | 5 sec | |
| Extension | 74 | 2 min | |
| Storing | 10 | overnight (14 hours) | |

TABLE 3-continued

Reaction solution composition

| Component | Concentration of undiluted solution | Mixing Amount µL | Final concentration |
|---|---|---|---|
| $H_2O$ | | 6.4 | |
| Dash Buffer | 10× | 1.0 | 1× |
| dNTP | 2 mM | 1.0 | 0.2 mM |
| KOD Dash | 2.5 u/µL | 0.2 | 0.05 u/µL |
| T7 primer | 10 µM | 0.2 | 0.2 µM |
| T3 primer | 10 µM | 0.2 | 0.2 µM |
| Colony soln. | | 1.0 | |
| Total | | 10.0 | |

From the colonies on the dish plate, ten colonies were selected at random and cells cultured of each colony were suspended in 70 µL of water (DDW). The suspension of cultured cells was treated at 95° C. of for 5 minutes. The solution containing the vectors isolated from the cells was used as a colony solution in the reaction solution.

After the PCR reaction was completed, 3 µL was sampled from the reaction solution (10 µL) including an amplification product and it was subjected to electrophoresis on 0.7% gel to analyze the existence and the range of the size of PCR amplification product corresponding to cDNA fragments. As for the cDNA library prepared as above, PCR amplification product corresponding to cDNA fragments was found out in five colonies among 10 colonies selected at random. Accordingly, it was judged that the ratio of the clones having a vector in which cDNA fragment was actually inserted among the transformed strains was about 50%.

Selection of Clone Retaining a cDNA Encoding the Fluorescent Protein Derived from Red Copepoda by Expression Cloning Method The number of genes encoding of the protein derived from Red Copepoda included in the cDNA library prepared is assumed to be $3 \times 10^4$. In the meantime, when the total number of colonies $3 \times 10^5$ cfu are grown, $1.5 \times 10^5$ cfu of the colony having a vector in which the cDNA fragment was inserted will be expected to be contained among those based on such a ratio of 50% therefor. When it assumes that the number of genes included in the cDNA library is $3 \times 10^4$ and that each of the genes is contained by occurrence frequency on the same order, the existence of about five colonies per each coding gene is expected in this case. Although the variation in occurrence frequency of the clone mainly reflects the ratio of the corresponding mRNA being present in the origin, it has been presumed that as for the colony of the transformed strain into which cDNA encoding the target fluorescent protein is inserted, at least 2-3 colony will be found out.

In addition, it has been reported that most of the GFP known heretofore are produced as mature GFP having fluorescent performance when expressed in host E. coli. There may be a good possibility that the fluorescent protein derived from Red Copepoda will be also produced as mature fluorescent protein possessing fluorescent performance when expressed in host E. coli.

Based on the above consideration, colony formation was performed by culturing the transformed strain which holds a cDNA library on plurality of dish plates with a culture medium LB/Car at least on the conditions which generate $1.5 \times 10^5$ or more colonies in total.

The glycerol added culture solution, which has been stocked by freezing at −80° C., was thawed, culture medium component SOC was added to form a culture solution of 2000

μL in total. 1 μL of the culture solution was sampled therefrom, 100 μL of culture medium component SOC was added, and the mixture obtained was inoculated on 9 cmφ dish plate to culture it at 37° C. overnight (for 14 hours). The total volume of the remaining culture medium was inoculated on LB/Car mediums prepared on 11 sheets of 15 cmφ dish plate to culture those at 37° C. overnight (for 14 hours).

153 colonies were generated from 1 μL of the culture solution on 9 cmφ dish plate. On the other hand, the total number of colonies summed up of those on 11 sheets of 15 cmφ dish plates reached at least $1.5 \times 10^5$ or more colonies. Therefore, it is inferred that the number of colonies generated in total may range from 153×2000, about $3.0 \times 10^5$ to $1.5 \times 10^5$.

As a result of investigating the existence of the colony, which emits fluorescence, over the colonies on 11 sheets of 15 cmφ dish plates in total, one colony which emits fluorescence under irradiation with ultraviolet light of the Dark Reader was found out. The colony, which emits fluorescence, was picked up to suspend it in 5 mL of the culture medium LB/Car, and then the suspension was diluted to 1/10 with this culture medium. 100 μL of the diluted solution of cells was inoculated on culture medium LB/Car, which was prepared on 15 cmφ dish plate, and secondary screening was conducted for the colony which emits fluorescence. After culturing at 37° C. overnight (for 14 hours), the colonies formed on 15 cmφ dish plate were observed under irradiation with ultraviolet light of the Dark Reader, and 80 to 90% of the colonies among them exhibited fluorescence.

In this secondary screening, four fluorescence positive colonies were sampled at random among the plurality of colonies that particularly exhibited clear fluorescence (fluorescence positive). These fluorescence positive colonies were suspended in 5 mL of the culture medium LB/Car respectively and cultured at 37° C. for 9 hours. Each of the culture solution of the four fluorescence positive colonies obtained was stored in freezing as a clone culture solution (containing 15% glycerol).

Replication and Purification of the Plasmid Vector being Introduced into the Selected Clone The plasmid vectors being introduced were replicated and purified from the four clones selected according to the following procedure.

In the system using host *E. coli* TOP10 where cDNA library was introduced, each of four colonies (clone), which were selected as a colony which emits fluorescence by the two-stage screening, was respectively suspended in 5 mL of the culture medium LB/Car, and cultured at 37° C. for 8 hours. The culture solution was subjected to centrifugation (5000×g) to take out the cells.

The plasmid was separated and purified from the taken out cells using a commercially available plasmid purifying kit: QIAGEN plasmid purification kit (product of QIAGEN). To the cells collected, 0.375 mL of P1 solution attached to the purifying kit was added and dispersed well by vortex. To this cell dispersion, 0.375 mL of P2 solution attached was added and mixed up. The mixture was allowed to stand still at room temperature (20° C.) for 5 minutes. Subsequently, 0.525 mL of N3 solution attached was added and mixed. After the treatment for cell disruption, centrifugation (11,000 rpm) was performed at 4° C. for 15 minutes, and a soluble fraction (supernatant) containing plasmid DNA was separated and collected.

The soluble fraction (supernatant) containing plasmid DNA was applied to QIAprep 4 column of the purifying kit. Centrifugation (15,000 rpm) was performed at 4° C., and the liquid layer was removed. 0.5 mL of PB was added and washed, and 0.75 mL of PE was added and washed succeedingly. Finally, centrifugation (15,000 rpm) was performed at 4° C. for 1 minute, and the washing solution was removed. The plasmid adsorbed on QIAprep of the purifying kit was eluted by 30 μL of Elute Buffer (EB) and collected. 2 μL from 30 μL of the solution containing the purified plasmid was diluted to a 50-fold diluted solution by adding 98 μL of distilled water.

The evaluation results of the DNA concentration contained in the solution containing a purified plasmid for each clone are summarized in Table 4.

TABLE 4

| Sample | $OD_{260}$ | $OD_{280}$ | $OD_{320}$ | Dilution Ratio | DNA concentration μg/μL | Total Volume μL | Amount of DNA μg | $OD_{260}/OD_{280}$ |
|---|---|---|---|---|---|---|---|---|
| No. 1 | 0.367 | 0.181 | <0.001 | ×50 | 0.920 | 28 | 25.76 | 2.02 |
| No. 2 | 0.337 | 0.168 | <0.001 | ×50 | 0.845 | 28 | 23.66 | 2.00 |
| No. 3 | 0.318 | 0.160 | <0.001 | ×50 | 0.798 | 28 | 22.33 | 1.98 |
| No. 4 | 0.371 | 0.181 | <0.001 | ×50 | 0.928 | 28 | 25.97 | 2.05 |

Nucleotide Sequence Analysis of cDNA Fragments in Selected Clones

The results of colony RCR has revealed that said four kinds of clones have cDNA fragments of the same nucleotide length in the plasmid vector carried therein. First, PCR amplification of the cDNA portion inserted into the plasmid vector was carried out according to the following procedures.

The solution, which contains the plasmid vector collected and purified from the selected clones, was adjust in concentration so that the DNA concentration might be 500 ng/μL. Then, by means of a commercially available DNA sample preparation kit: BigDye Terminator Cycle Sequecing Ready Reaction Kit with AmpliTaq polymerase, used were this purified plasmid vector as a template and as forward primer T7 primer: GTAATACGACTCACTATAGGGC  (SEQ ID NO: 10)

which corresponds to the nucleotide sequence of T7 promoter site; and as reverse primer

```
                TTAATTGGGAGTGATTTCCC      (SEQ ID NO: 11)

3 primer: AATTAACCCTCACTAAAGGG           (SEQ ID NO: 12)
``` which is complementary to the nucleotide sequence of T3 promoter site, to prepare the sample for nucleotide sequence analysis from the region containing cDNA inserted into the plasmid vector.

The temperature conditions and reaction solution composition used for DNA chain extension reaction are shown in Table 5.

TABLE 5

Reaction solution composition

| Component | Concentration of undiluted solution | Mixing Amount Ratio μL |
|---|---|---|
| Terminator Reaction Mix | | 1.0 |
| Template DNA | 500 ng/μL | 1.0 |
| Primer | 1 μM | 0.8 |
| DDW | | 2.2 |
| Total | | 5.0 |

Temperature conditions used for DNA chain extension reaction:
Used equipment: Mastercycler Gradient

| Cycle operation | Temperature °C. | Duration | |
|---|---|---|---|
| Denaturing | 96 | 1 min | |
| Denaturing | 96 | 10 sec | 25 times |
| Annealing | 50 | 5 sec | Ramp. Rate 1° C./s |
| Extension | 60 | 4 min | Ramp. Rate 1° C./s |
| Storing | 4 | overnight (14 hours) | |

Purifying the prepared sample for nucleotide sequence analysis was carried out according to the following procedures.

The prepared sample solution was transferred from each tube for reaction to another 0.5 mL tube. A liquid formed by mixing 0.5 μL of 3 M sodium acetate aqueous solution and 12.5 μL of 95% ethanol in a ratio per 5 μL of the sample solution was separately prepared in a 1.5 mL tube beforehand. The sample solution collected beforehand was placed in the 1.5 mL tube. After mixing uniformly, the mixture was allowed to stand still for 10 minutes under ice-cooling, and thereby the DNA fragment contained was ethanol precipitated (separated). Centrifugation (14,000 rpm) was performed for 20 minutes to settle the DNA fragments precipitated, and the supernatant was removed. Subsequently, 125 μL of 70% ethanol was added and the DNA fragments precipitated were rinsed. Centrifugation (14,000 rpm) was performed again for 5 minutes to settle the separated DNA fragments, and the supernatant was removed by suction. The pellet of the remaining DNA fragments precipitated was dried.

The purified DAN fragments for analysis sample were re-dispersed in Template suppressor Reagent (TSR). The mixture was mixed by vortex, and then centrifuged to collect the liquid. The liquid was heated at 95° C. for 2 minutes to split DNA fragments into single strand DNA's, and then ice-cooled. After vortexing, centrifugation was performed and the plasmid used as a template was made to precipitate. After this processing of splitting off the plasmid used as a template, it was stocked at −20° C. Then, the DAN fragments for analysis sample were subjected to a commercially available sequencer: ABI PRISM 3100 Genetic Analyzer to perform nucleotide sequence analysis.

The result of sequence analysis from the 5'-terminus and the result of sequence analysis from the 3'-terminus were combined together, and the nucleotide sequence of the cDNA fragment prepared from mRNA encoding the fluorescent protein derived from Red Copepoda was well determined.

(Recombinant Expression of the Fluorescent Protein Derived from Red Copepoda)
Insertion of the Gene of Fluorescent Protein Derived from Red Copepoda into Plasmid pET101/D-TOPO First, based on the above-mentioned nucleotide sequence, forward primer and reverse primer for PCR

```
forward primer: pET-UP1(28 mer)
5-CACCATGACAACCTTCAAAATCGAGTCC           (SEQ ID NO:
                                              4)

reverse primer: SalI-LP1(35 mer);
5-CTCGTCGACCTACATGTCTCTTGGGGCGCTGTTGA (SEQ ID NO:
                                              5)
``` wherein in order to introduce a cleavage site for SalI restriction enzyme at the 3-terminus thereof, a corresponding nucleotide sequence is appended thereto, were prepared and products of PCR amplification were obtained using as a template the vector collected from the isolated clone. The temperature conditions and reaction solution composition used for PCR reaction are shown in Table 6.

TABLE 6

Temperature conditions used for PCR reaction:
Used equipment: Mastercycler Gradient (eppendorf)

| Cycle operation | Temperature °C. | Duration | |
|---|---|---|---|
| Denaturing | 96 | 1 min | |
| Annealing | 60 | 5 sec | |
| Extension | 68 | 45 sec | 25 times |
| Denaturing | 96 | 5 sec | |
| Extension | 68 | 45 sec | |
| Storing | 10 | overnight (14 hours) | |

Reaction solution composition

| Component | Concentration of undiluted solution | Mixing amount μL | Final concentration |
|---|---|---|---|
| H₂O | | 6.4 | |
| Pyro Buffer | 10× | 1.0 | 1× |
| dNTP | 2 mM | 1.0 | 0.2 mM |
| Pyrobest DNA Pol. | 5 u/μL | 0.1 | 0.05 u/μL |
| pET-UP1 | 10 μM | 0.2 | 0.2 μM |
| SalI-LP1 | 10 μM | 0.2 | 0.2 μM |
| Template plasmid | 1 μg/μM | 1.0 | 0.1 μg/μM |
| Total | | 10.0 | |

Purifying the prepared PCR amplification product was carried out according to the following procedures.

After carrying out a PCR reaction using of 25 μL of the reaction solution for each, reaction solutions resulted by 3-time run in total were combined to obtain 2 μL of the reaction solution, subjected to electrophoresis on 1% agarose gel, and the PCR amplification product of the object molecular weight 673 bp was confirmed.

Subsequently, Product DNA was concentrated from the reaction solution by MinElute method. After 5 volumes of PB buffer was added per 1 volume of the reaction solution (73 μL), the mixture was vortexed and transferred to MinElute column. Centrifugation was performed for 30 seconds to settle the precipitated DNA fragments and the supernatant was removed. The precipitated DNA was washed by 0.7 mL of PE buffer, and centrifugation (15,000 rpm) was performed for one minute. Furthermore, 10 μL of EB buffer was added and it was allowed to stand still for 1 minute at room temperature. Then, centrifugation (15,000 rpm) was performed for 1 minute, and the supernatant was collected.

After 2 μL of 10× loading dye liquid was added to the collected DNA solution, 12 μL of DNA solution for each lane was subjected to electrophoresis on a 1.0% TAE agarose gel. The target band of 688 bp was excised from the gel. The excised gel pieces were put in into a 1.5 mL eppendorf tube, and the DNAs were collected.

As shown in FIG. 2, the purified double stranded DNA was inserted into a commercially available plasmid pET101/D-TOPO (product of Invitrogen), and an expression vector: pET101-NFP of the fluorescent protein derived from the Red Copepoda was prepared.

In addition, expression vector of fluorescent protein: pGEX6P1-NFP was also prepared in which the fluorescent protein derived from the Red Copepoda was linked via a linker sequence containing a cleavage site for endopeptidase Factor Xa to the C-terminus of glutathion S-transferase (GST), a fusion partner. That is, utilizing as forward and reverse primers for PCR

```
    forward primer: GST-UP1(43 mer)
                                (SEQ ID NO: 6)
5-CGAATTCATCGAAGGCCGCATGACAACCTTCAAAATCGAGTCC (SEQ ID NO: 4)
            5-CACCATGACAACCTTCAAAATCGAGTCC
``` wherein to the above-mentioned pET-UP1 (28 mer) were appended a partial sequence of ATCGAAGGCCGC (SEQ ID NO: 7) encoding the amino acid sequence for the cleavage site of protease Factor Xa and a corresponding nucleotide sequence GAATTC in order to introduce a cleavage site by Eco RI restriction enzyme at the 5'-terminus; and

```
reverse primer: SalI-LP1(35 mer)
5-CTCGTCGACCTACATGTCTCTTGGGGCGCTGTTGA  (SEQ ID NO:
                                                   5)
``` wherein in order to introduce a cleavage site for SalI restriction enzyme at the 3'-terminus thereof, a corresponding nucleotide sequence is appended thereto;
PCR amplification products were obtained by using as a template the vectors collected from the isolated clone. The temperature conditions and reaction solution composition used for PCR reaction are shown in Table 7.

TABLE 7

Temperature conditions used for PCR reaction:
Used equipment: Mastercycler Gradient (eppendorf)

| Cycle operation | Temperature °C. | Duration | |
|---|---|---|---|
| Denaturing | 96 | 1 min | |
| Annealing | 60 | 5 sec | |
| Extension | 68 | 45 sec | 25 times |
| Denaturing | 96 | 5 sec | |
| Extension | 68 | 45 sec | |
| Storing | 10 | overnight (14 hours) | |

Reaction solution composition

| Ingredient | Concentration of undiluted solution | Mixing amount μL | Final concentration |
|---|---|---|---|
| H₂O | | 6.4 | |
| Pyro Buffer | 10× | 1.0 | 1× |

TABLE 7-continued

| dNTP | 2 mM | 1.0 | 0.2 mM |
|---|---|---|---|
| Pyrobest DNA Pol. | 5 u/μL | 0.1 | 0.05 u/μL |
| GST-UP1 | 10 μM | 0.2 | 0.2 μM |
| SalI-LP1 | 10 μM | 0.2 | 0.2 μM |
| Template plasmid | 1 μg/μM | 1.0 | 0.1 μg/μM |
| Total | | 10.0 | |

Purifying the prepared PCR amplification product was carried out referring to the aforementioned procedures.

First, after carrying out a PCR reaction using of 25 μL of the reaction solution for each, reaction solutions resulted by 3-time run in total were pooled. 2 μL of the reaction solution sampled therefrom was subjected to electrophoresis on 1% agarose gel to confirm the PCR amplification product of the object molecular weight 688 bp (19+660+9). Procedures and conditions for subsequent separation and purification were the same.

The purified double strand DNA was once incorporated into pCR4 Blunt-TOPO (product of Invitrogen), and clone selection was performed with the selection marker. Each selected clone was cultured and this clone plasmid pCR4 Blunt-NFP was proliferated. After culturing, the plasmid contained was purified therefrom to check the molecular weight size and the nucleotide sequence of the DNA fragment inserted therein. Subsequently, as shown in FIG. 3, Eco RI/Sal I fragment of the insert DNA of 688 bp, which contained ORF (open reading frame) following the aforementioned portion encoding of the cleavage sequence of the Factor Xa, was inserted into a commercially available plasmid vector: PGEX-6P-1 (product of Amersham Biosciences) for protein expression of the fusion type with a GST tag to construct an expression vector: pGEX6P1-NFP of the fluorescent protein NFP with a GST tag.

(Fluorescence Performance of the Recombinant Expression Product of Fluorescent Protein NFP Derived from Red Copepoda)

First, E. coli was transformed using the expression vector: pET101-NFP of the fluorescent protein NFP shown in FIG. 2. Clone selection was carried out on the obtained transformed E. coli with use of an ampicillin resistance gene as a selection marker.

As for the clone selected, IPTG was employed to induce expression of the inserted gene through a promoter derived from the vector pET101/D-TOPO, and check was kept on expression of the fluorescent protein 2 hours and 4 hours after the induction. In addition, the fact that the recombinant fluorescent protein, which was expressed after expression induction by IPTG expression, was processed in the form a mature protein was confirmed by the occurrence of fluorescence in the colony of the transformed strain under irradiation of ultraviolet light.

The cultured cells of the transformed strain cultured were collected 4 hours after the expression induction with IPTG. After the cultured cells were crushed, SDS-PAGE analysis was performed on the proteins contained in a soluble fraction (cytoplasmic components) and insoluble fraction (membrane components) which were separated by centrifugation (15,000 rpm; 18,800×g), respectively. Consequently, a new band of molecular weight 25 kDa was found in the soluble fraction (cytoplasmic components) of the transformed E. coli. That is, the molecular weight of the fluorescent protein derived from the Red Copepoda was predicted to be 24.7 kDa from the deduced amino acid sequence mentioned above, which is coincident with the new band of molecular weight 25 kDa shown in the results of SDS-PAGE analysis of FIG. 4.

The transformed E. coli carrying the expression vector of the fluorescent protein derived from the Red Copepoda: pET101-NFP was subjected to large-scale culturing, and isolation and purification of the fluorescent protein recombinant was tried.

The isoelectric point (pI) of the fluorescent protein recombinant was predicted (calculated) beforehand based on the deduced amino acid sequence thereof, and it was calculated as pI=6.50. With reference to the result, the soluble fraction (cytoplasmic components) was applied to an anion exchange column: HiTrap DEAE FF (product of Amersham Biosciences), and the fluorescent protein recombinant was collected in fractions with 4.8-8.8% B buffer under the following elution conditions:
A buffer: 20 mM Tris-HCl pH 7.6
B buffer: 1 M NaCl in A buffer;
linear gradient with B buffer of 0-20% (NaCl concentrations of 0 to 200 mM).

Then, the collected fractions were preliminarily concentrated by means of VIVASPIN20 under condition of MW 10,000 cut. This concentrated sample was applied to gel filtration: HiLoad 16/60 Superdex 200 pg (product of Amersham Biosciences), and the fluorescent protein recombinant was purified and collected as a fluorescent fraction having a molecular weight of 100 kDa or less under the elution condition: A buffer 20 mM Tris-HCl pH 7.6. SDS-PAGE analysis performed at this stage showed a state where the aimed fluorescent protein recombinant was almost purified as shown in FIG. 5.

It was confirmed that the solution of purified protein sample at this stage emitted a yellowish green fluorescence under irradiation with Dark Reader light (wavelength range: 420 nm to 500 nm), as shown in FIG. 6. Of course, fluorescence was not observed in the control sample, which is prepared by subjecting a soluble fraction (cytoplasmic components) of host E. coli to the same purifying treatment. A fluorescence spectrum and an excitation spectrum was actually measured using the purified protein solution sample at this stage. The maximum peak was found at the wavelength of 507 nm in the excitation spectrum measured while monitoring the fluorescence intensity at the wavelength of 500 nm, as shown in FIG. 7. On the other hand, as for the fluorescence spectrum measured with excitation at the wavelength of 508 nm, a fluorescence having a maximum peak with a wavelength of 518 nm and covering over a yellow zone (wavelength range: 570 nm to 590 nm) was confirmed.

Figure 10:
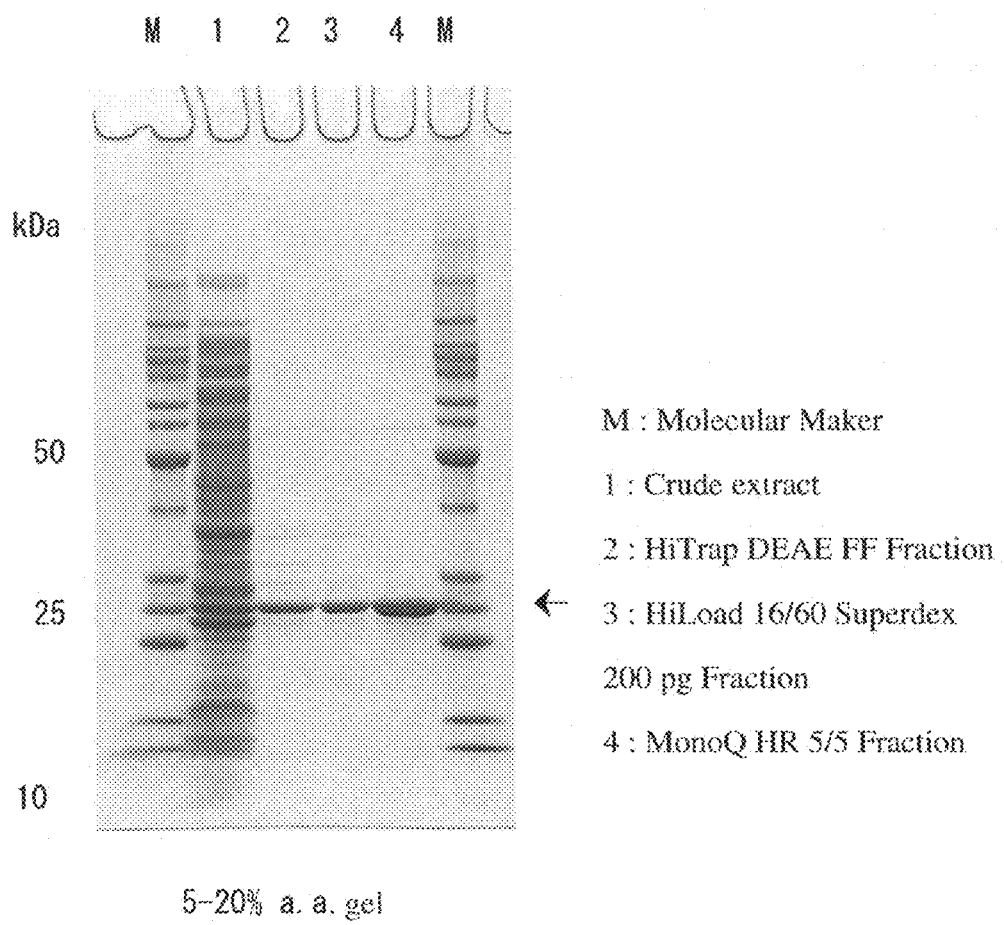
FIG. 10 shows the result of the SDS-PAGE analysis that shows the purification steps as for the fluorescent protein recombinant expression product derived from Red Copepoda of the present invention.

Furthermore, a protein solution sample filtered with gel filtration was applied to MonoQ HR 5/5 column (product of Amersham Biosciences), and the purified fluorescent protein recombinants were collected into B buffer 12.0-14.0% fractions under the elution condition:
A buffer: 20 mM Tris-HCl pH 7.6,
B buffer: 1 M NaCl in A buffer;
linear gradient with B buffer of 10-20% (100-200 mM NaCl concentration). The results of SDS-PAGE analysis for each protein solution sample of the steps in the aforementioned process for purifying the recombinant expression product of the fluorescent protein derived from Red Copepoda are shown in FIG. 10.

In addition, E. coli was transformed using expression vector: pGEXGP1-NFP for the fluorescent protein with a GST tag shown in FIG. 3. The obtained transformed E. coli, host E. coli (negative control), and the isolated clone (positive control), in which cDNA encoding the fluorescent protein derived from the Red Copepoda was inserted into cloning vector: pBluescript II SK, were cultured on a culture medium, respectively. As shown in FIG. 8, when each colony was observed under irradiation with Dark Reader light (wavelength range: 420 nm to 500 nm), the colony of the obtained transformed E. coli emitted fluorescence, and it was confirmed that the fluorescent protein with a GST tag was expressed therein. Moreover, it is also confirmed that when recombinant expression thereof was made in the form of a fusion protein linked with another protein through a proper linker sequence, translated peptide chain is processed to form a mature fluorescent protein having a fluorescence performance through cyclization of the internal tripeptide site and its subsequent oxidization, which forms a fluorophore.

(Temperature Dependency of the Fluorescence Performance of the Recombinant Expression Product of Fluorescent Protein NFP Derived from Red Copepoda)

The purified fluorescent protein NFP recombinant prepared by the above-mentioned technique was subjected to incubation treatment at various temperatures to evaluate the dependency of the fluorescence performance on the treatment temperature according to the following test method.

Incubation treatment is performed each for 10 μL of solution, in which the purified fluorescent protein NFP recombinant at a protein concentration of 0.577 mg/mL is contained in 20 mM Tris-HCl pH 8.5 buffer, for 10 minutes at temperatures: 4, 20, 30, 37, 45, 50, 55, 60, 65, 70, 75 or 80° C. The solution containing NFP recombinant is ice-cooled (0° C.) after the treatment. 192.5 μL of 20 mM Tris-HCl pH 8.5 buffer is added to 10 μL each of the solution ice-cooled (0° C.) to dilute it, resulting in the diluted solution at the final protein concentration of 20 μg/mL. This diluted solution was used to measure the fluorescence spectrum of the fluorescent protein NFP recombinant therein under excitation at a wavelength of 507 nm with a spectrofluorometer manufactured by Hitachi.

Incidentally, the fluorescence spectrum measured in a diluted solution containing the fluorescent protein NFP recombinant without subjected to incubation treatment exhibits the maximum peak at a wavelength of 518 nm. The fluorescence spectrum observed for said diluted solution containing the fluorescent protein NFP recombinant, which has been subjected to incubation treatment at the various temperatures, is measured on the basis of this fluorescence spectrum measured for the fluorescent protein NFP recombinant, which has not been subjected to incubation treatment. The fluorescence intensity at the wavelength of 517 nm in the fluorescence spectrum measured was plotted against the treatment temperature used at the step of said incubation treatment on the abscissa axis, and the plot shown in FIG. 11 was obtained.

Figure 11:
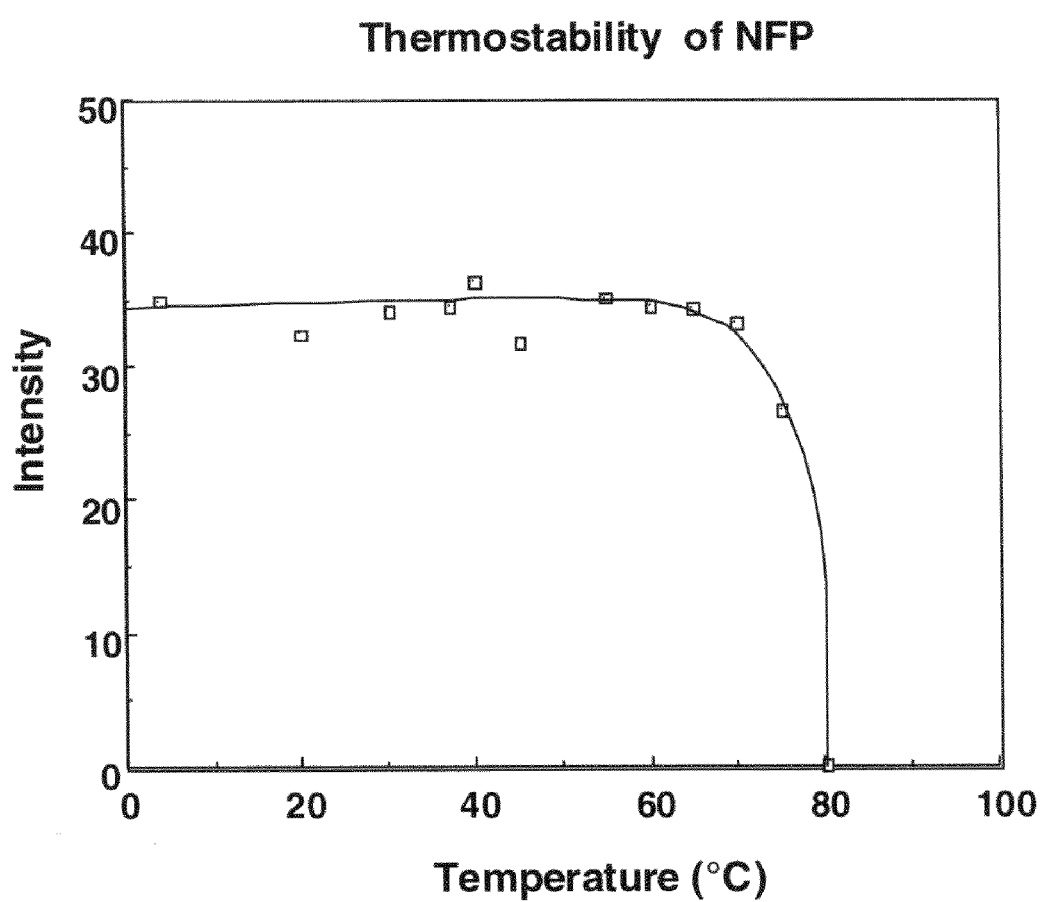
FIG. 11 shows the stability of the fluorescence performance (fluorescence intensity measured at a wavelength of 517 nm) exhibited by the fluorescent protein recombinant expression product against the heat-treatment at variety of temperatures, wherein the fluorescent protein recombinant expression product derived from Red Copepoda of the present invention was subjected to incubation treatment at each temperature.

In the plot shown in FIG. 11, no deterioration in the fluorescence performance of the fluorescent protein NFP recombinant is found when ice-cooling (0° C.) is carried out after the incubation treatment at treatment temperature in the range of 70° C. or lower. On the other hand, reduction in the fluorescence performance of the fluorescent protein NFP recombinant is observed in such a case that ice-cooling (0° C.) is performed after incubation treatment at treatment temperature of 75° C. or higher. Therefore, as long as ice-cooling (0° C.) is carried out after incubation treatment at a treatment temperature in the range of 70° C. or lower, there will be no deterioration of the fluorescence performance due to the structural change resulted from heat denaturation, and it is estimated that the fluorescent protein NFP recombinant shows high temperature-stability in said temperature range.

(Agent Resistance of the Fluorescence Performance of the Recombinant Expression Product of Fluorescent Protein NFP Derived from Red Copepoda)

The purified fluorescent protein NFP recombinant prepared by the above-mentioned technique is subjected to incubation treatment in the presence of various reagents (agents) to evaluate the stability of the fluorescence performance against the action of the various agents according to the following test method.

To 10 μL each of solution which contains the purified fluorescent protein NFP recombinant at a protein concentration of 0.577 mg/mL in 20 mM Tris-HCl pH 8.5 buffer, 192.5 μL each of various kinds of reagent (agent) solution listed below is added to form solutions of a final protein concentration of 20 μg/mL which contain the agent. These agent-containing solutions are subjected to incubation treatment under ice-cooling (0° C.) for 10 minutes. After the treatment, the agent-containing solutions were used to measure the fluorescence spectrum of the fluorescent protein NFP recombinant therein under excitation at a wavelength of 507 nm with a spectrofluorometer manufactured by Hitachi.

| Composition of various kinds of reagent (agent) solution | |
| --- | --- |
| 20 mM Tris-HCl pH 8.5 | Buffer solution for Dilution |
| 1% SDS | Solution containing 1% SDS (sodium dodecyl sulfate) |
| 10 mM 2-Me | Solution containing 10 mM 2-mercaptoethanol |
| 100 mM 2-Me | Solution containing 100 mM 2-mercaptoethanol |
| 10 mM DTT | Solution containing 10 mM DTT (dithiothreitol) |
| 100 mM DTT | Solution containing 100 mM DTT (dithiothreitol) |
| 4 M GuHCl | Solution containing 4 M GuHCl (guanidine hydrochloride) |
| 6 M GuHCl | Solution containing 6 M GuHCl (guanidine hydrochloride) |
| 6 M Urea | Solution containing 6 M urea |
| 8 M Urea | Solution containing 8 M urea |
| 1% PFA | Solution containing 1% PFA (perfluoroacetic acid) |
| 10% TCA | Solution containing 10% TCA (trichloroacetic acid) |
| 3.6% HCHO | Solution containing 3.6% HCHO (formaldehyde) |
| 10% HCHO | Solution containing 10% HCHO (formaldehyde) |
| 36% HCHO | Solution containing 36% HCHO (formaldehyde) |
| 50% EtOH | Solution containing 50% EtOH (ethanol) |
| 100% EtOH | 100% EtOH (absolute ethanol) |
| 50% MtOH | Solution containing 50% MtOH (methanol) |
| 100% MtOH | 100% MtOH (methanol) |
| 50% Aceton | Solution containing 50% acetone |
| 100% Aceton | 100% acetone |

Figure 12:
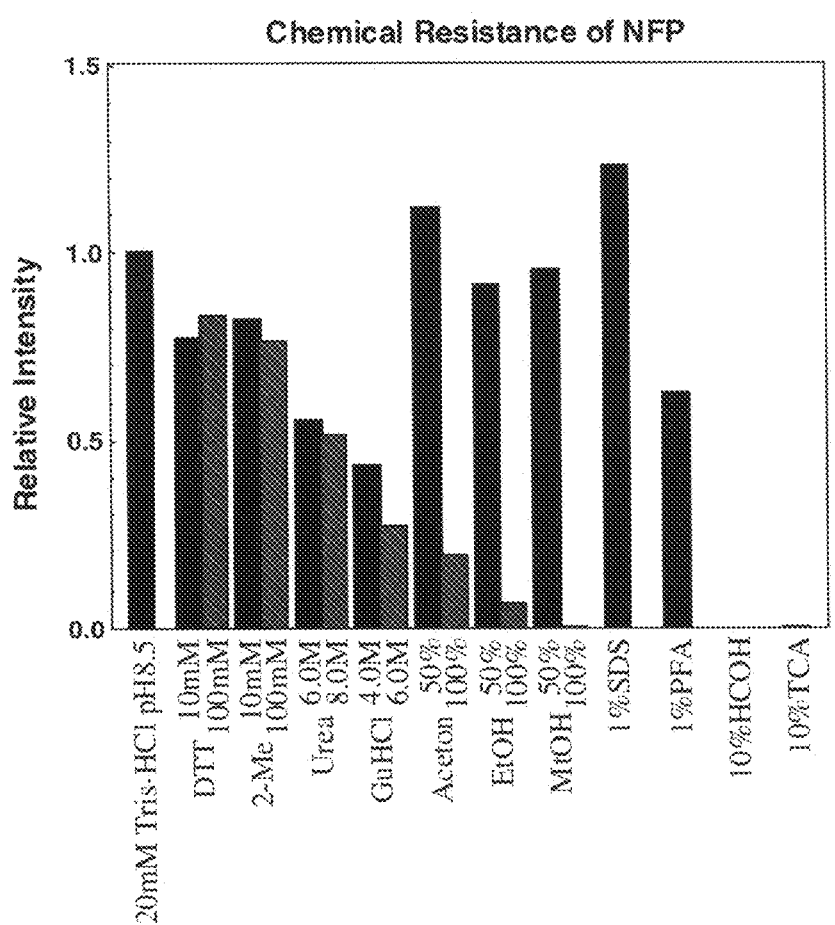
FIG. 12 shows the stability of the fluorescence performance (fluorescence intensity measured at a wavelength of 517 nm) exhibited by the fluorescent protein recombinant expression product against the action of various agents wherein the fluorescent protein recombinant expression product derived from Red Copepoda of the present invention was subjected to incubation treatment in the presence of each reagent (agent)

FIG. 12 shows fluorescence performance (fluorescence intensity measured at a wavelength of 517 nm) exhibited by the fluorescent protein recombinant expression product after the fluorescent protein recombinant expression product derived from Red Copepoda of the present invention is subjected to incubation treatment in the presence of various reagents (agents) by the relative value on the basis of the fluorescence performance exhibited in the case of adding the dilution buffer (20 mM Tris-HCl pH 8.5 buffer) thereto.

When the organic solvent is added and the solvate water molecules covering the fluorescent protein recombinant expression product are removed, the fluorescence performance exhibited by the fluorescent protein recombinant expression product is markedly reduced. If guanidine hydrochloride or urea, which have a function of protein denaturing agent, acts thereon, the fluorescence performance exhibited by the fluorescent protein recombinant expression product is considerably lessened. However, the action of about 1% of SDS (sodium dodecyl sulfate) does not affect the fluorescence performance exhibited by the fluorescent protein recombinant expression product at all.

The fluorescence performance thereof suffers some deterioration under the action of 2-mercaptoethanol or DTT (dithiothreitol), which has an action of reducing the Cys-Cys bond in protein.

(pH Dependency of the Fluorescence Performance of the Recombinant Expression Product of Fluorescent Protein NFP Derived from Red Copepoda)

The purified fluorescent protein NFP recombinant prepared by the above-mentioned technique is subjected to incubation treatment in the solution supplemented with various pH buffer solutions to evaluate pH dependency of the fluorescence performance thereof according to the following test method.

To 10 μL each of a solution containing the purified fluorescent protein NFP recombinant at a protein concentration of 0.577 mg/mL in 20 mM Tris-HCl pH 8.5 buffer, 192.5 μL each of various kinds of buffer solution listed below is added to prepare a diluted solution at the final protein concentration of 20 μg/mL having a pH adjusted by the buffer solution. These solutions exhibiting various pH are subjected to incubation treatment under ice-cooling (0° C.) for 10 minutes. After the treatment, these solutions having various pH are used to measure the fluorescence spectrum of the fluorescent protein NFP recombinant therein under excitation at a wavelength of 507 nm with a spectrofluorometer manufactured by Hitachi.

Buffer Solution for pH Adjustment:

| | |
| --- | --- |
| pH 3.0 | Glycine-HCl |
| pH 3.5 | Glycine-HCl |
| pH 4.0 | Acetate |
| pH 4.5 | Acetate |
| pH 5.0 | Acetate |
| pH 5.5 | Acetate |
| pH 6.0 | Phosphate |
| pH 7.0 | HEPES |
| pH 8.0 | Tris-HCl |
| pH 8.5 | Tris-HCl |
| pH 8.9 | Tris-HCl |
| pH 10.0 | Carbonate |
| pH 10.5 | Carbonate |
| pH 11.0 | Carbonate |
| pH 11.5 | Phosphate-NaOH |
| pH 12.0 | Phosphate-NaOH |
| pH 12.5 | Phosphate-NaOH |
| pH 13.0 | Phosphate-NaOH |
| pH 13.6 | NaOH |

Figure 13:
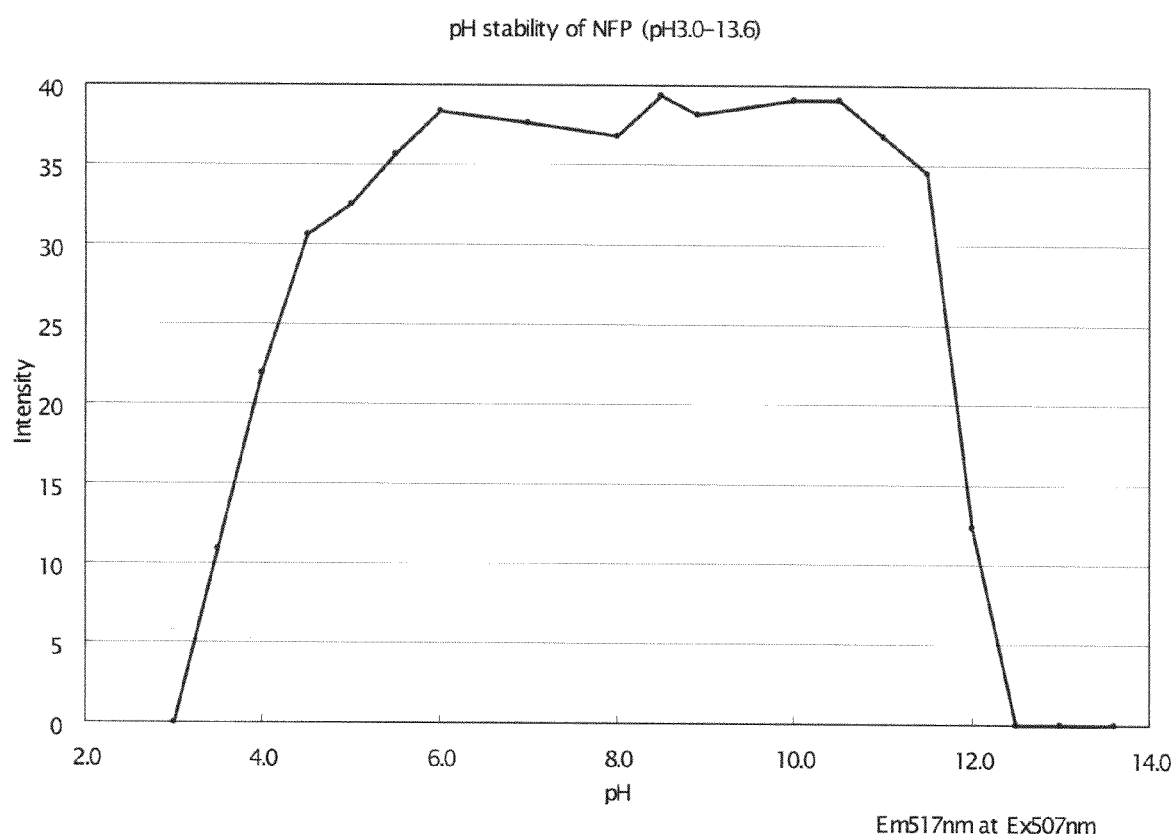
FIG. 13 is the stability of the fluorescence performance (fluorescence intensity measured at a wavelength of 517 nm) exhibited by the fluorescent protein recombinant expression product against pH during treatment, wherein the fluorescent protein recombinant expression product derived from Red Copepoda of the present invention was subjected to incubation treatment at the pH of various buffer solutions.

FIG. 13 shows the results plotting the fluorescence performance (fluorescence intensity measured at a wavelength of 517 nm) exhibited by the fluorescent protein recombinant expression product versus the pH value being adjusted by the various buffer solutions, which are measured after the fluorescent protein recombinant expression product derived from Red Copepoda of the present invention has been subjected to incubation treatment in pH adjusted with various buffer solutions. It is confirmed that the fluorescence performance exhibited by the fluorescent protein recombinant expression product shows high stability at least within the range of pH 6.0 to 11.0.

Figure 14:
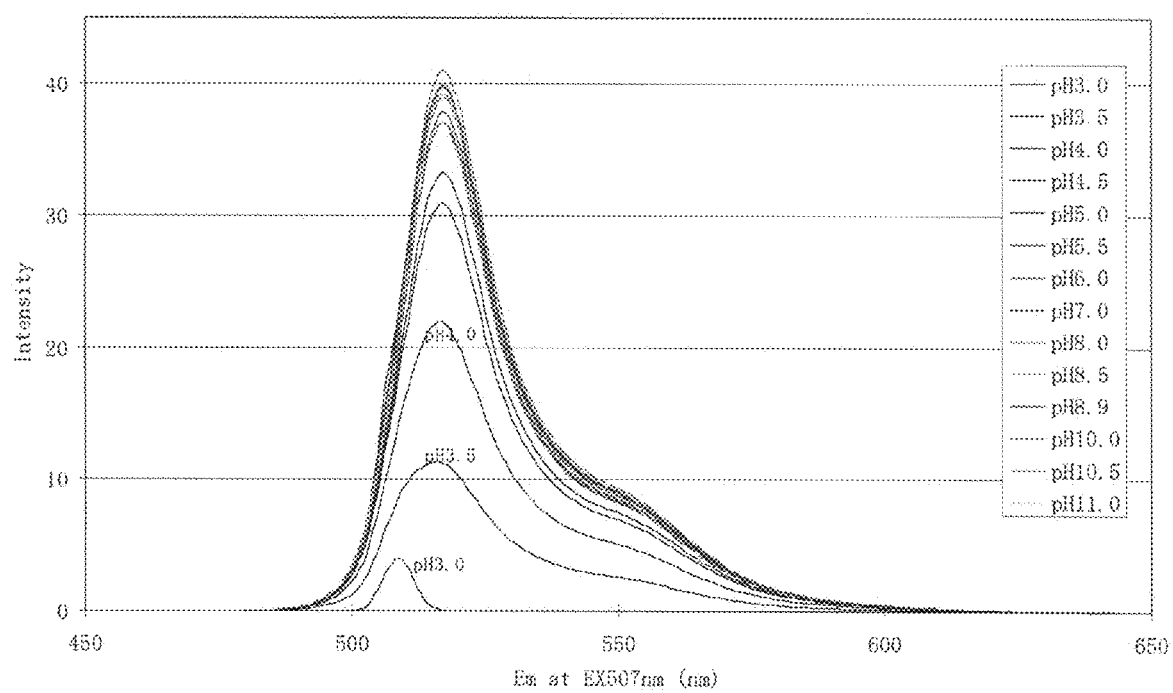
FIG. 14 is the stability of the fluorescence performance (fluorescence spectrum measured under excitation at an excitation wavelength of 507 nm) exhibited by the fluorescent protein recombinant expression product against pH during treatment, wherein the fluorescent protein recombinant expression product derived from Red Copepoda of the present invention was subjected to incubation treatment at the pH of various buffer solutions.

FIG. 14 shows series of the measurement results in the range of pH 3.0 to pH 11.0 collectively, as for the fluorescence spectra of the fluorescent protein NFP recombinant, which have been measured in the solution of various kinds pH in the course of said evaluation process. Although the fluorescence intensity for the maximum peak measured at a wavelength of 517 nm varies, it is confirmed that the relative shape of the fluorescence spectrum of the fluorescent protein NFP recombinant is maintained substantially at least within the range of pH 3.5 to pH 11.0.

(Resistance to Ultraviolet Light Irradiation for the Fluorescence Performance of the Recombinant Expression Product of Fluorescent Protein NFP Derived from Red Copepoda)

The purified fluorescent protein NFP recombinant prepared by the above-mentioned technique is subjected to treatment of long-time irradiation with ultraviolet light at a wavelength of 302 nm to evaluate the stability of the fluorescence performance thereof over said prolonged irradiation with ultraviolet light according to the following test method.

The solution containing the purified fluorescent protein NFP recombinant at a protein concentration of 0.577 mg/mL in 20 mM Tris-HCl pH 8.5 buffer is subjected to continuous irradiation for 60 minutes with ultraviolet light of a wavelength of 302 nm, at the radiation intensity of 7300 $\mu W/cm^2$. In the meantime, samples each in an amount of 10 $\mu L$ are sampled before the start of irradiation (irradiation duration: 0 minute), at the time points of 0, 1, 5, 10, 15, 30 and 45 minutes passing after the irradiation starts, and at the time when the irradiation ends (irradiation duration 60 minutes). To 10 $\mu L$ each of the sample solutions collected, 192.5 $\mu L$ each of 20 mM Tris-HCl pH 8.5 buffer is added to dilute it, resulting in the diluted solution at the final protein concentration of 20 $\mu g/mL$. These diluted solutions are used to measure the fluorescence spectrum of the fluorescent protein NFP recombinant therein under excitation at a wavelength of 507 nm with a spectrofluorometer manufactured by Hitachi.

Figure 17:
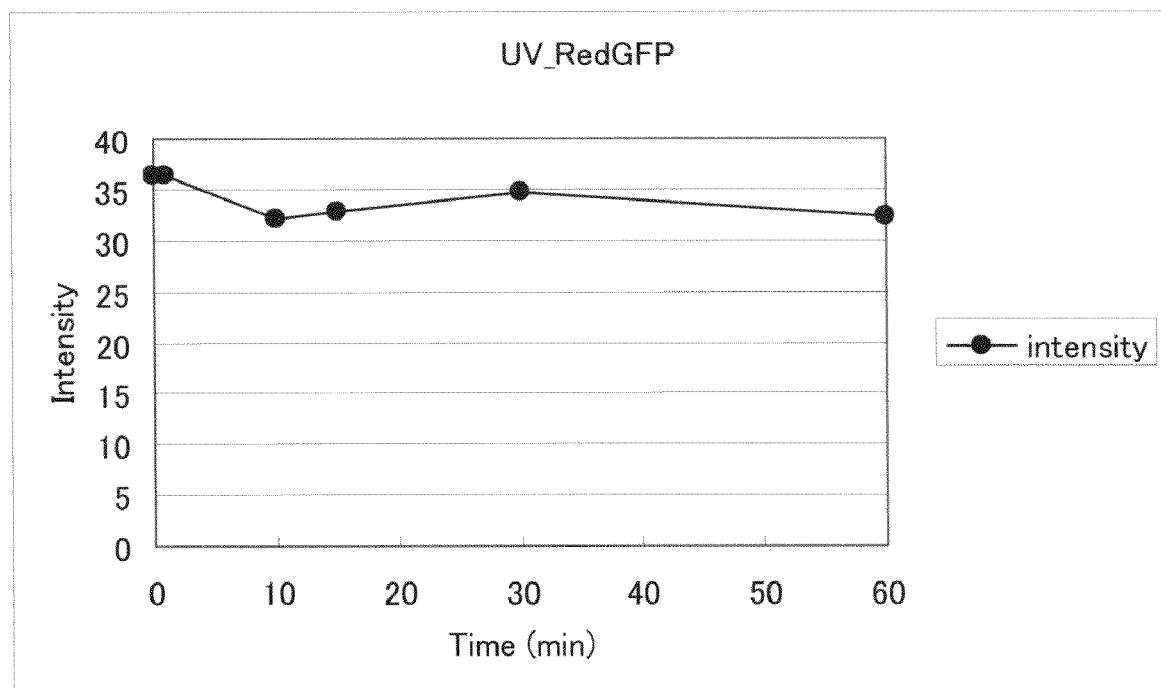
FIG. 17 shows the stability of the fluorescence performance (fluorescence intensity measured at a wavelength of 517 nm) exhibited by the fluorescent protein recombinant expression product against ultraviolet irradiation, wherein the fluorescent protein recombinant expression product derived from Red Copepoda of the present invention was subjected to treatment of irradiation with ultraviolet of a wavelength of 302 nm for various irradiation times.

FIG. 17 shows the fluorescence performance (fluorescence intensity measured at a wavelength of 517 nm) exhibited by the fluorescent protein recombinant expression product, which was measured after the fluorescent protein recombinant expression product derived from Red Copepoda of the present invention was subjected to the continuous irradiation with the ultraviolet light at a wavelength of 302 nm, by the relative value on the basis of the fluorescence performance thereof before irradiation. It is confirmed by the results shown in FIG. 17 that the fluorescent protein recombinant expression product derived from Red Copepoda is not substantially degraded at least when the duration for continuous irradiation with the ultraviolet light at a wavelength of 302 nm is within the range of 60 minutes or shorter.

(Recombinant Expression of the Fluorescent Protein Derived from Red Copepoda in Human Cell)

Figure 15:
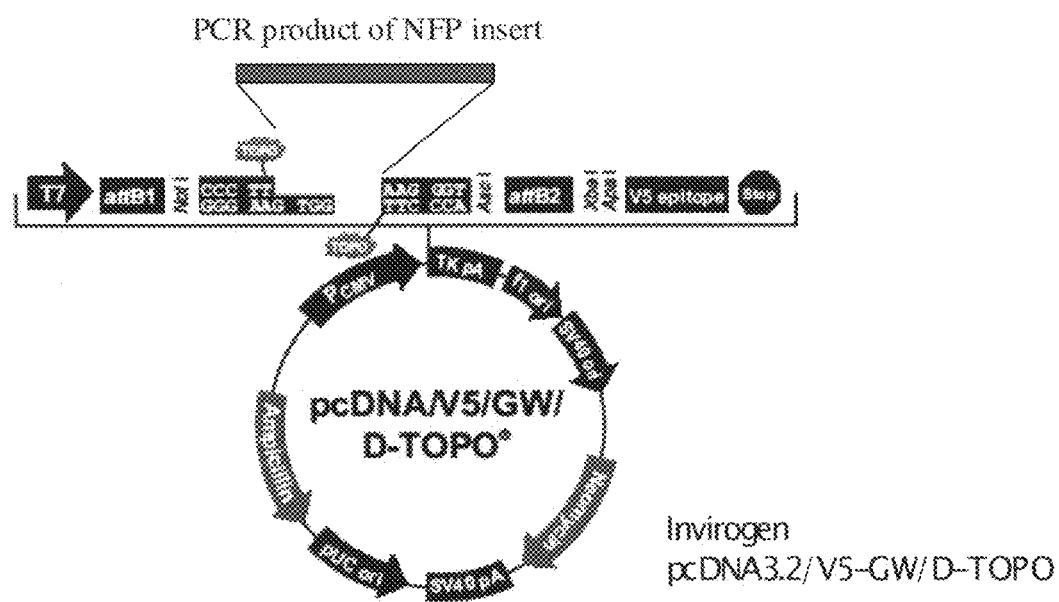
FIG. 15 is a drawing illustrating the composition of the expression vector for the fluorescent protein derived from the Red Copepoda, which was used for recombinant expression within the HeLa cell of the fluorescent protein recombinant expression product derived from Red Copepoda of the present invention, wherein the coding gene (660 bp) of the fluorescent protein derived from the Red Copepoda was inserted into the cloning site of commercially available plasmid pcDNA3.2/V5-GW/D-TOPO (product of Invitrogen) (the cloning site sequence is set forth in SEQ ID NO:22)

Insertion of the Gene of the Fluorescent Protein Derived from Red Copepoda into Plasmid pcDNA3.2/V5-GW/D-TOPO Following the aforementioned procedures for construction of the expression vector of the fluorescent protein derived from Red Copepoda: pET101-NFP, purified double strand DNA, which was prepared by the PCR method based on the coding gene of the fluorescent protein NFP derived from Red Copepoda, was inserted into the cloning site of a commercially available plasmid pcDNA3.2/V5-GW/D-TOPO (product of Invitrogen) to construct an expression vector for expressing the fluorescent protein derived from the Red Copepoda in a human cell. FIG. 15 shows the constitution of the expression vector constructed for expressing the fluorescent protein NFP derived from the Red Copepoda in human cell. In this case, the double strand DNA fragment inserted into the expression vector has the same nucleotide sequence as the coding gene of the fluorescent protein NFP derived from Red Copepoda, and codon conversion which suits to the codon selection in human is not effected. That is, it is the same as the double strand DNA fragment inserted into the above-mentioned expression vector: pET101-NFP.

Recovery and purification of the prepared plasmid were performed using a commercially available plasmid purifying kit; QIAGEN Plasmid Maxi Kit (product of QIAGEN).

Introduction to the Hela Cell of the Expression Vector for Expressing the Fluorescent Protein Derived from the Red Copepoda in Human Cell The purified expression vector for expressing the fluorescent protein NFP derived from the Red Copepoda in a human cell is introduced into a HeLa cell by applying the PolyFect Transfection method. As for the host HeLa cell, those cultured up to 70% of confluent state on a 100-mm dish using a serum-added culture medium (DMEM +10% FBS +100 $\mu g/mL$ Kanamycin) are used. On the other hand, 6.0 $\mu L$ of an expression vector plasmid solution (DNA content: 5 ng/mL) is added to 50.0 $\mu L$ of a commercially available reagent solution for PolyFect Transfection: PolyFect Transfection Reagent (product of QIAGEN), and this mixed solution is agitated for 10 minutes. After PolyFect Transfection treatment, HeLa cells are held at 37° C. under atmosphere of 5% $CO_2$, subjected to incubation treatment for 24 to 48 hours to recover the cell damage associated with the treatment and culture.

Figure 16:
FIG. 16 is a fluorescence image print-out which shows the results obtained by observing the fluorescence in a HeLa cell under the fluorescence microscope, which was resulted from the fluorescent protein recombinant expression product expressed under the control of the promoter derived from CMV, after culturing a transformed HeLa cell for 18 hours which was produced by injecting the expression vector of the fluorescent protein derived from the Red Copepoda shown in the above-mentioned FIG. 15 into a HeLa cell.

When recombinant expression of the fluorescent protein NFP derived from the Red Copepoda was induced in the HeLa cells to which was introduced the expression vector, as is shown in FIG. 16 as an example, fluorescence which originates in the whole cell at the recombinant of the fluorescent protein NFP was observed in a part of the culturing cells. That is, it is clearly shown that in the HeLa cells of human origin, translation was made to the recombinant of the fluorescent protein NFP based on the coding gene of the fluorescent protein NFP derived from Red Copepoda, and followed by processing thereof in a cell post to the translation, resulting to the mature fluorescent protein NFP.

Therefore, it has been proved that the coding gene of the fluorescent protein NFP derived from Red Copepoda can be fully used in the in vitro culture system which uses various kinds of cell line derived from humans without codon conversion to adjust the codon usage in human cells, as a coding gene for an in vivo fluorescent marker protein which can express in the host human cell.

Furthermore, it has been proved as follows that the fluorescent protein NFP derived from Red Copepoda can actually be used as an in vivo fluorescent marker protein, which can be expressed within a host cell.

It is to be proved that a fusion protein formed by linking the fluorescent protein NFP derived from the Red Copepoda to the N-terminus of the target protein can be expressed in a host cell in a quite similar manner to the fluorescent marker protein EGFP currently used widely, and that the fusion protein to be expressed maintains the fluorescence performance which originates in the fluorescent protein NFP in the portion of the N-terminus and the function of the target protein in the portion of the C-terminus.

With use of a commercially available plasmid vector; pGFP-Actin (5820 bp: product of BD Biosciences Clontech) for the expression of a fusion protein of commonly used fluorescent marker protein EGFP and human cytoplasmic β-actin; and a commercially available plasmid vector pGFP-Tub (6045 bp: product of BD Biosciences Clontech) for the expression of a fusion protein of EGFP and human α-tubulin; the code sequence portion of the fluorescent marker protein EGFP therein is replaced by the code sequence of the fluorescent protein NFP derived from the Red Copepoda to construct vectors for recombinant expression of the fusion protein of NFP-Human cytoplasmic β-actin (1128 bp, 375aa) and of a fusion protein NFP-Human α-tubulin (in frame with RedGFP 1356 bp, 451aa) according to the following procedure.

PCR amplification is performed using a forward primer NFP NheI/Kozak-UP1 and a reverse primer NFP SalI-LP1 described below so that kozak sequence (GCCACC) is appended immediately before the start codon for the coding gene of the fluorescent protein NFP derived from Red Copepoda, and a recognition sequence (GCTAGC) for restriction enzyme NheI is provided in an upstream non-translating region thereof; and further the stop codon is removed, and a nucleotide sequence (T CCG GAC TCA GAT) (SEQ ID NO:13) constituting a part of the coding nucleotide sequence for the linker sequence is appended as well as a recognition sequence (GTCGAC) for restriction enzyme SalI is provided downstream thereto.

```
NFP NheI/Kozak-UP1 48 mer
                                        (SEQ ID NO: 14)
5'-CCA GCT AGC GCT ACG GTC GCC ACC ATG ACA ACC TTC

AAA ATC GAG TCC-3'

NFP SalI-LP1 45 mer
                                        (SEQ ID NO: 15)
5'-AAA GTC GAC ATC TGA GTC CGG ACA TGT CTC TTG GGG

CGC TGT TGA-3'
```

The code sequence portion of fluorescent marker protein EGFP, which is included in commercially available plasmid vectors pGFP-Actin as well as pGFP-Tub, is digested by restriction enzymes NheI and XhoI to remove it therefrom. On the other hand, the obtained PCR product (703 bp) is digested at the sites for the restriction enzyme NheI and SalI, which are newly introduced. The obtained DNA fragment and each of the vector fragments from the plasmid vectors being digested by the restriction enzymes are ligated together to construct the vectors for recombinant expression of fusion proteins, respectively. Purification of the prepared plasmid was performed using commercially available purifying kit; EndoFree Plasmid Maxi Kit (Qiagen).

The nucleotide sequence analysis for the two kinds of the expression vectors constructed was performed to verify the nucleotide sequence of the inserted DNA fragment derived from the PCR product and the linking portion, and it was confirmed that the code sequence of the fluorescent protein NFP derived from the Red Copepoda and the target protein on the side of the C-terminus were linked through the linker part without a frame shift. Particularly the amino acid sequence of the linker part prepared between the fluorescent protein NFP derived from the Red Copepoda and the object protein on the side of the C-terminus was a partial amino acid sequence

```
SGLRCRA                                 (SEQ ID NO: 16)

7a.a. encoded by
TCC GGA CTC AGA TGT CGA GCT             (SEQ ID NO: 17)

AGG CCT GAG TCT ACA GCT CGA             (SEQ ID NO: 18)
``` which was formed by ligating a nucleotide sequence (T CCG GAC TCA GAT) (SEQ ID NO:13) contained in the above-mentioned reverse primer: NFP SalI-LP1, and the cleavage site in the recognition sequence (GTCGAC) for the restriction enzyme SalI downstream thereof with the above-mentioned vector fragment.

According to the above-mentioned transfection procedure, the vector for the expression in a human cell of each fusion protein is introduced into a HeLa cell, respectively by applying the PolyFect Transfection method. When cultured for 16 hours after the genetic recombination, those emitting fluorescence among the cultured HeLa cells were found out. Microscopic observation revealed that the distribution of the fluorescence intensity in a cell is localized in the HeLa cells into which the vector for expressing the fusion protein with the fluorescent protein NFP mentioned above was introduced, whereas uniform fluorescence from the whole cell was observed in the aforementioned HeLa cells into which the vector for expression of just the fluorescent protein NFP was introduced.

That is, the fluorescent protein NFP derived from Red Copepoda which is capable of recombinant expression in the form of a fusion protein in human cell, and after translation, constitutes the portion on the N-terminus and exhibits fluorescence performance through proper folding. In the meantime, it is observed as a localized fluorescence intensity distribution due to the localization of β-actin or α-tubulin which is used as C-terminus portion therein. This result is a proof indicating that the coding gene of the fluorescent protein NFP derived from Red Copepoda can be actually used as a coding gene of an in vivo fluorescent marker protein which can be expressed in the host cell in the in vitro culture system using various kinds cell lines of human origin.

INDUSTRIAL APPLICABILITY

The fluorescent protein of the present invention can be used an in vivo fluorescent marker protein which can be expressed in the host cell in the in vitro culture system using a mammalian cell.

The invention claimed is:

1. A purified DNA molecule encoding a fluorescent protein consisting of the amino acid sequence of SEQ ID NO: 1,
wherein the fluorescent protein consisting of the amino acid sequence of SEQ ID NO: 1 has a fluorescence spectrum having a maximum peak with a wavelength of 518 nm and an excitation spectrum having a maximum peak of wavelength of 507 nm,
wherein a fluorescence performance of the fluorescent protein is due to the fluorescent core of the fluorescent protein, which fluorescent core is post-translationally formed from the $G^{55}Y^{56}G^{57}$ tripeptide site in SEQ ID NO:1 through cyclization and subsequent oxidation.

2. The purified DNA molecule according to claim 1, wherein the nucleotide sequence of the DNA molecule is the nucleotide sequence of SEQ ID NO: 2 which nucleotide sequence is identical to the open reading frame (ORF) of the nucleotide sequence of SEQ ID NO: 3 encoding the corresponding amino acid sequence of SEQ ID NO: 1.

3. The purified DNA molecule according to claim 1, wherein the DNA molecule is a cDNA containing a region encoding the amino acid sequence of SEQ ID NO: 1 and prepared from mRNA of a fluorescent protein from a copepod taxonomically classified to *Chiridius Poppei*, wherein the nucleotide sequence of the cDNA is the nucleotide sequence of SEQ ID NO: 3.

4. A recombinant pBluescript II SK expression vector characterized in that the vector is formed by cloning the cDNA of SEQ ID NO: 3 comprising an ORF that encodes the amino acid sequence of SEQ ID NO: 1 and prepared from mRNA of a fluorescent protein from a copepod taxonomically classified to *Chiridius Poppei*.

* * * * *

UNITED STATES PATENT AND TRADEMARK OFFICE
CERTIFICATE OF CORRECTION

PATENT NO. : 8,043,850 B2  Page 1 of 1
APPLICATION NO. : 12/204557
DATED : October 25, 2011
INVENTOR(S) : Frederick I. Tsuji et al.

It is certified that error appears in the above-identified patent and that said Letters Patent is hereby corrected as shown below:

In the Specification

Column 18, Line 57: delete "frozen" and insert -- frozed --
Column 21, Line 18: delete "3 L" and insert -- 3 μL --
Column 21, Line 62: delete "200 L" and insert -- 200 μL --
Column 22, Line 54: delete "509" and insert -- 50% --
Column 23, Line 6: delete "U/muL)" and insert -- U/μL) --
Column 23, Line 15: after "for" insert -- 5 --
Column 23, Line 63: delete "3 L" and insert -- 3 μL --
Column 24, Line 5: delete "0.76" and insert -- 0.7% --
Column 28, Line 58: delete "3" and insert -- T3 --
Column 30, Line 16: delete "3-terminus" and insert -- 3'-terminus --

Signed and Sealed this
Twenty-third Day of September, 2014

Michelle K. Lee
*Deputy Director of the United States Patent and Trademark Office*

SEQUENCE LISTING

```
<160> NUMBER OF SEQ ID NOS: 22

<210> SEQ ID NO 1
<211> LENGTH: 219
<212> TYPE: PRT
<213> ORGANISM: Chiridius poppei

<400> SEQUENCE: 1

Met Thr Thr Phe Lys Ile Glu Ser Arg Ile His Gly Asn Leu Asn Gly
1               5                   10                  15

Glu Lys Phe Glu Leu Val Gly Gly Gly Val Gly Glu Glu Gly Arg Leu
```

```
                    20                  25                  30
Glu Ile Glu Met Lys Thr Lys Asp Lys Pro Leu Ala Phe Ser Pro Phe
             35                  40                  45

Leu Leu Ser His Cys Met Gly Tyr Gly Phe Tyr His Phe Ala Ser Phe
         50                  55                  60

Pro Lys Gly Thr Lys Asn Ile Tyr Leu His Ala Ala Thr Asn Gly Gly
 65                  70                  75                  80

Tyr Thr Asn Thr Arg Lys Glu Ile Tyr Glu Asp Gly Gly Ile Leu Glu
                 85                  90                  95

Val Asn Phe Arg Tyr Thr Tyr Glu Phe Asn Lys Ile Ile Gly Asp Val
            100                 105                 110

Glu Cys Ile Gly His Gly Phe Pro Ser Gln Ser Pro Ile Phe Lys Asp
        115                 120                 125

Thr Ile Val Lys Ser Cys Pro Thr Val Asp Leu Met Leu Pro Met Ser
    130                 135                 140

Gly Asn Ile Ile Ala Ser Ser Tyr Ala Arg Ala Phe Gln Leu Lys Asp
145                 150                 155                 160

Gly Ser Phe Tyr Thr Ala Glu Val Lys Asn Asn Ile Asp Phe Lys Asn
                165                 170                 175

Pro Ile His Glu Ser Phe Ser Lys Ser Gly Pro Met Phe Thr His Arg
            180                 185                 190

Arg Val Glu Glu Thr His Thr Lys Glu Asn Leu Ala Met Val Glu Tyr
        195                 200                 205

Gln Gln Val Phe Asn Ser Ala Pro Arg Asp Met
    210                 215

<210> SEQ ID NO 2
<211> LENGTH: 660
<212> TYPE: DNA
<213> ORGANISM: Chiridius poppei

<400> SEQUENCE: 2
atgacaacct tcaaaatcga gtcccggatc catggcaacc tcaacgggga gaagttcgag      60
ttggttggag gtggagtagg tgaggagggt cgcctcgaga ttgagatgaa gactaaagat     120
aaaccactgg cattctctcc cttcctgctg tcccactgca tgggttacgg gttctaccac     180
ttcgccagct cccaaagggg gactaagaac atctatcttc atgctgcaac aaacggaggt     240
tacaccaaca ccaggaagga gatctatgaa gacggcggca tcttgaggt caacttccgt      300 tacacttacg agttcaacaa gatcatcggt gacgtcgagt gcattggaca tggattccca     360
agtcagagtc cgatcttcaa ggacacgatc gtgaagtcgt gtccacggt ggacctgatg      420 ttgccgatgt ccgggaacat catcgccagc tcctacgcta gagccttcca actgaaggac     480
ggctctttct acacggcaga agtcaagaac aacatagact caagaatcc aatccacgag      540 tccttctcga gtcggggcc catgttcacc cacagacgtg tcgaggagac tcacaccaag      600
gagaaccttg ccatggtgga gtaccagcag gttttcaaca gcgccccaag agacatgtag     660

<210> SEQ ID NO 3
<211> LENGTH: 782
<212> TYPE: DNA
<213> ORGANISM: Chiridius poppei

<400> SEQUENCE: 3
agaacactca gtgtatccag ttttccgtcc tactacaaac atgacaacct tcaaaatcga      60
gtcccggatc catggcaacc tcaacgggga gaagttcgag ttggttggag gtggagtagg     120
```

-continued

```
tgaggagggt cgcctcgaga ttgagatgaa gactaaagat aaaccactgg cattctctcc      180
cttcctgctg tcccactgca tgggttacgg gttctaccac ttcgccagct tcccaaaggg      240
gactaagaac atctatcttc atgctgcaac aaacggaggt tacaccaaca ccaggaagga      300
gatctatgaa gacggcgcca tcttggaggt caacttccgt tacacttacg agttcaacaa      360
gatcatcggt gacgtcgagt gcattggaca tggattccca agtcagagtc cgatcttcaa      420
ggacacgatc gtgaagtcgt gtcccacggt ggacctgatg ttgccgatgt ccgggaacat      480
catcgccagc tcctacgcta gagccttcca actgaaggac ggctctttct acacggcaga      540
agtcaagaac aacatagact tcaagaatcc aatccacgag tccttctcga agtcggggcc      600
catgttcacc cacagacgtg tcgaggagac tcacaccaag gagaaccttg ccatggtgga      660
gtaccagcag gttttcaaca cgcccccaag agacatgtag aatgtggaac gaaacctttt      720
tttctgatta ctttctctgt tgactccaca ttcggaactt gtataaataa gttcagttta      780
aa                                                                    782
```

```
<210> SEQ ID NO 4
<211> LENGTH: 28
<212> TYPE: DNA
<213> ORGANISM: Artificial Sequence
<220> FEATURE:
<223> OTHER INFORMATION: PCR primer pET-UP1

<400> SEQUENCE: 4
caccatgaca accttcaaaa tcgagtcc                                         28

<210> SEQ ID NO 5
<211> LENGTH: 35
<212> TYPE: DNA
<213> ORGANISM: Artificial Sequence
<220> FEATURE:
<223> OTHER INFORMATION: PCR primer SalI-LP1

<400> SEQUENCE: 5
ctcgtcgacc tacatgtctc ttggggcgct gttga                                 35

<210> SEQ ID NO 6
<211> LENGTH: 43
<212> TYPE: DNA
<213> ORGANISM: Artificial Sequence
<220> FEATURE:
<223> OTHER INFORMATION: PCR primer GST-UP1

<400> SEQUENCE: 6
cgaattcatc gaaggccgca tgacaacctt caaaatcgag tcc                        43

<210> SEQ ID NO 7
<211> LENGTH: 12
<212> TYPE: DNA
<213> ORGANISM: Artificial Sequence
<220> FEATURE:
<223> OTHER INFORMATION: coding region for protease Factor Xa cleavage
      site

<400> SEQUENCE: 7
atcgaaggcc gc                                                          12

<210> SEQ ID NO 8
<211> LENGTH: 222
<212> TYPE: PRT
<213> ORGANISM: Artificial Sequence
<220> FEATURE:
<223> OTHER INFORMATION: Humanized Copepoda fluorescent protein
```

<400> SEQUENCE: 8

```
Met Pro Ala Met Lys Ile Glu Cys Arg Ile Thr Gly Thr Leu Asn Gly
1               5                   10                  15

Val Glu Phe Glu Leu Val Gly Gly Gly Glu Gly Thr Pro Glu Gln Gly
            20                  25                  30

Arg Met Thr Asn Lys Met Lys Ser Thr Lys Gly Ala Leu Thr Phe Ser
        35                  40                  45

Pro Tyr Leu Leu Ser His Val Met Gly Tyr Gly Phe Tyr His Phe Gly
    50                  55                  60

Thr Tyr Pro Ser Gly Tyr Glu Asn Pro Phe Leu His Ala Ile Asn Asn
65                  70                  75                  80

Gly Gly Tyr Thr Asn Thr Arg Ile Glu Lys Tyr Glu Asp Gly Gly Val
                85                  90                  95

Leu His Val Ser Phe Ser Tyr Arg Tyr Glu Ala Gly Arg Val Ile Gly
            100                 105                 110

Asp Phe Lys Val Val Gly Thr Gly Phe Pro Glu Asp Ser Val Ile Phe
        115                 120                 125

Thr Asp Lys Ile Ile Arg Ser Asn Ala Thr Val Glu His Leu His Pro
    130                 135                 140

Met Gly Asp Asn Val Leu Val Gly Ser Phe Ala Arg Thr Phe Ser Leu
145                 150                 155                 160

Arg Asp Gly Gly Tyr Tyr Ser Phe Val Val Asp Ser His Met His Phe
                165                 170                 175

Lys Ser Ala Ile His Pro Ser Ile Leu Gln Asn Gly Gly Pro Met Phe
            180                 185                 190

Ala Phe Arg Arg Val Glu Glu Leu His Ser Asn Thr Glu Leu Gly Ile
        195                 200                 205

Val Glu Tyr Gln His Ala Phe Lys Thr Pro Ile Ala Phe Ala
    210                 215                 220
```

<210> SEQ ID NO 9
<211> LENGTH: 669
<212> TYPE: DNA
<213> ORGANISM: Artificial Sequence
<220> FEATURE:
<223> OTHER INFORMATION: Coding seqeunce for humanized Copepoda fluorescent protein

<400> SEQUENCE: 9

```
atgcccgcca tgaagatcga gtgccgcatc accggcaccc tgaacggcgt ggagttcgag      60
ctggtgggcg gcggagaggg caccccccgag cagggccgca tgaccaacaa gatgaagagc     120
accaagggcg ccctgacctt cagccctac ctgctgagcc acgtgatggg ctacggcttc       180
taccacttcg gcacctaccc cagcggctac gagaaccct tcctgcacgc catcaacaac       240
ggcggctaca ccaacacccg catcgagaag tacgaggacg gcggcgtgct gcacgtgagc      300
ttcagctacc gctacgaggc cggccgcgtg atcggcgact tcaaggtggt gggcaccggc      360
ttccccgagg acagcgtgat cttcaccgac aagatcatcc gcagcaacgc caccgtggag      420
cacctgcacc ccatgggcga taacgtgctg gtgggcagct tcgcccgcac cttcagcctg      480
cgcgacggcg gctactacag cttcgtggtg acagccaca tgcacttcaa gagcgccatc       540
caccccagca tcctgcagaa cggggggccc atgttcgcct tccgccgcgt ggaggagctg      600
cacagcaaca ccgagctggg catcgtggag taccagcacg ccttcaagac cccgatcgca      660
ttcgcctga                                                              669
```

```
<210> SEQ ID NO 10
<211> LENGTH: 22
<212> TYPE: DNA
<213> ORGANISM: Artificial Sequence
<220> FEATURE:
<223> OTHER INFORMATION: PCR primer T7

<400> SEQUENCE: 10
gtaatacgac tcactatagg gc                                              22

<210> SEQ ID NO 11
<211> LENGTH: 20
<212> TYPE: DNA
<213> ORGANISM: Artificial Sequence
<220> FEATURE:
<223> OTHER INFORMATION: T3 promoter sequence

<400> SEQUENCE: 11
ttaattggga gtgatttccc                                                 20

<210> SEQ ID NO 12
<211> LENGTH: 20
<212> TYPE: DNA
<213> ORGANISM: Artificial Sequence
<220> FEATURE:
<223> OTHER INFORMATION: PCR primer T3

<400> SEQUENCE: 12
aattaaccct cactaaaggg                                                 20

<210> SEQ ID NO 13
<211> LENGTH: 13
<212> TYPE: DNA
<213> ORGANISM: Artificial Sequence
<220> FEATURE:
<223> OTHER INFORMATION: coding sequence for linker peptide

<400> SEQUENCE: 13
tccggactca gat                                                        13

<210> SEQ ID NO 14
<211> LENGTH: 48
<212> TYPE: DNA
<213> ORGANISM: Artificial Sequence
<220> FEATURE:
<223> OTHER INFORMATION: PCR primer NFP NheI/Kozak-UP1

<400> SEQUENCE: 14
ccagctagcg ctacggtcgc caccatgaca accttcaaaa tcgagtcc                  48

<210> SEQ ID NO 15
<211> LENGTH: 45
<212> TYPE: DNA
<213> ORGANISM: Artificial Sequence
<220> FEATURE:
<223> OTHER INFORMATION: PCR primer NFP SalI-LP1

<400> SEQUENCE: 15
aaagtcgaca tctgagtccg gacatgtctc ttggggcgct gttga                     45

<210> SEQ ID NO 16
<211> LENGTH: 7
<212> TYPE: PRT
<213> ORGANISM: Artificial Sequence
<220> FEATURE:
<223> OTHER INFORMATION: Linker peptide
```

-continued

```
<400> SEQUENCE: 16

Ser Gly Leu Arg Cys Arg Ala
1               5

<210> SEQ ID NO 17
<211> LENGTH: 21
<212> TYPE: DNA
<213> ORGANISM: Artificial Sequence
<220> FEATURE:
<223> OTHER INFORMATION: sequence encoding linker peptide

<400> SEQUENCE: 17
tccggactca gatgtcgagc t                                                   21

<210> SEQ ID NO 18
<211> LENGTH: 21
<212> TYPE: DNA
<213> ORGANISM: Artificial Sequence
<220> FEATURE:
<223> OTHER INFORMATION: sequence complementary to sequence encoding
      linker peptide

<400> SEQUENCE: 18
aggcctgagt ctacagctcg a                                                   21

<210> SEQ ID NO 19
<211> LENGTH: 15
<212> TYPE: DNA
<213> ORGANISM: Artificial Sequence
<220> FEATURE:
<223> OTHER INFORMATION: sequence of cloning site in plasmid
      pET101/D-TOPO

<400> SEQUENCE: 19
gggaagtggt tcccg                                                          15

<210> SEQ ID NO 20
<211> LENGTH: 22
<212> TYPE: PRT
<213> ORGANISM: Artificial Sequence
<220> FEATURE:
<223> OTHER INFORMATION: Protease cleavage site and multiple cloning
      site of plasmid pGEX

<400> SEQUENCE: 20

Leu Glu Val Leu Phe Gln Gly Pro Leu Gly Ser Pro Glu Phe Pro Gly
1               5                   10                  15

Arg Leu Glu Arg Pro His
            20

<210> SEQ ID NO 21
<211> LENGTH: 66
<212> TYPE: DNA
<213> ORGANISM: Artificial Sequence
<220> FEATURE:
<223> OTHER INFORMATION: nucleotide sequence encoding protease cleavage
      site and multiple cloning site of plasmid pGEX

<400> SEQUENCE: 21
ctggaagttc tgttccaggg gccccctggga tccccggaat tccgggtcg actcgagcgg         60 ccgcat                                                                    66

<210> SEQ ID NO 22
<211> LENGTH: 15
<212> TYPE: DNA
<213> ORGANISM: Artificial Sequence
```

```
<220> FEATURE:
<223> OTHER INFORMATION: cloning site of plasmid pcDNA/V5/GW/D-TOPO

<400> SEQUENCE: 22
gggaagtggt tccca                                                    15
```